(12) United States Patent
Manku et al.

(10) Patent No.: US 9,670,126 B2
(45) Date of Patent: Jun. 6, 2017

(54) METHODS OF MAKING 15-HYDROXY FATTY ACID DERIVATIVES

(71) Applicant: Dignity Sciences Limited, Dublin (IE)

(72) Inventors: Mehar Manku, Birmingham (GB); David Coughlan, Dublin (IE); Bill Downes, Dublin (IE)

(73) Assignee: DIGNITY SCIENCES LIMITED, Dublin (IE)

(*) Notice: Subject to any disclaimer, the term of this patent is extended or adjusted under 35 U.S.C. 154(b) by 0 days.

(21) Appl. No.: 14/527,601

(22) Filed: Oct. 29, 2014

(65) Prior Publication Data

US 2015/0119593 A1 Apr. 30, 2015

Related U.S. Application Data

(60) Provisional application No. 61/896,901, filed on Oct. 29, 2013.

(51) Int. Cl.
C07C 51/00 (2006.01)
C07C 59/42 (2006.01)
C07C 51/367 (2006.01)

(52) U.S. Cl.
CPC ............ *C07C 59/42* (2013.01); *C07C 51/367* (2013.01)

(58) Field of Classification Search
CPC ...................................................... C07C 51/00
USPC ......................................................... 554/154
See application file for complete search history.

(56) References Cited

PUBLICATIONS

M. B. W. Elshof et al: "Biocatalytic hydroxylation of linoleic acid in a double-fed batch system with lipoxygenase and cysteine", European Journal of LI PID Science and Technology., vol. 100, 1998, pp. 246-251.*

Hamberg M et al: "On the Specificity of the Oxygenation of Unsaturated Fatty Acids Catalyzed by Soybean Lipoxidase", Journal of Biological Chemistry, American Society for Biochemistry and Molecular Biology, US, vol. 242, Jan. 1, 1967, pp. 5329-5335.*

* cited by examiner

*Primary Examiner* — Deborah D Carr
(74) *Attorney, Agent, or Firm* — Perkins Coie LLP

(57) ABSTRACT

The present disclosure provides methods of making 15-hydroxy fatty acid derivatives, such as 15-(S)-hydroxyeicosatrienoic acid (HETrE or 15-(S)-HETrE) or 15(S)-hydroxyeicosapentaenoic acid (HEPE or 15(S)-HEPE) from the corresponding fatty acid (e.g., dihomo-γ-linolenic acid (DGLA) or eicosapentaenoic acid (EPA), respectively). In some embodiments, the method comprises contacting the fatty acid with an oxidizing agent (e.g., a lipoxygenase and oxygen) in the presence of a reducing agent (e.g., cysteine) to form the 15-hydroxy fatty acid derivatives in a single reaction vessel.

15 Claims, 22 Drawing Sheets

| | RT | Area | % Area | Height |
|---|---|---|---|---|
| 1 | 2.993 | 46635 | 0.07 | 1070 |
| 2 | 4.832 | 11147 | 0.02 | 531 |
| 3 | 5.289 | 97308 | 0.14 | 4943 |
| 4 | 7.750 | 18570 | 0.03 | 515 |
| 5 | 9.182 | 258621 | 0.38 | 5448 |
| 6 | 12.690 | 17486 | 0.03 | 633 |
| 7 | 21.123 | 285590 | 0.42 | 7095 |

| | RT | Area | % Area | Height |
|---|---|---|---|---|
| 8 | 30.547 | 65793189 | 96.07 | 926358 |
| 9 | 33.850 | 378341 | 0.55 | 5501 |
| 10 | 35.250 | 233040 | 0.34 | 2799 |
| 11 | 36.883 | 72403 | 0.11 | 1723 |
| 12 | 48.090 | 627126 | 0.92 | 8544 |
| 13 | 63.417 | 66262 | 0.10 | 9218 |
| 14 | 63.478 | 116763 | 0.17 | 10406 |
| 15 | 63.784 | 125880 | 0.18 | 15052 |
| 16 | 64.048 | 77996 | 0.11 | 13171 |
| 17 | 64.150 | 40038 | 0.06 | 6405 |
| 18 | 64.328 | 44133 | 0.06 | 4723 |
| 19 | 64.866 | 156552 | 0.23 | 20257 |
| 20 | 65.283 | 16740 | 0.02 | 1013 |

| Timepoint | Area% purity (252 nm) | Area% dimer impurity peak at RT ~12.2 mins |
|---|---|---|
| T=0 | 97.2 | 0.44 |
| T=1 hr | 97.2 | 0.44 |
| T=2 hr | 97.3 | 0.44 |
| T=3 hr | 97.2 | 0.44 |
| T=4 hr | 97.2 | 0.44 |
| T=6 hr | 97.1 | 0.44 |
| T=24 hr | 97.4 | 0.49 |
| T=48 hr | 97.5 | 0.49 |
| T=66 hr | 97.4 | 0.52 |
| T=112 hr | 97.4 | 0.64 |

Figure 15.

DGLA

Chemical Formula: $C_{20}H_{34}O_2$
Exact Mass: 306.26
Molecular Weight: 306.48
m/z: 306.26 (100.0%), 307.26 (22.1%), 308.26 (2.7%)

EDA

Chemical Formula: $C_{20}H_{36}O_2$
Exact Mass: 308.27
Molecular Weight: 308.50
m/z: 308.27 (100.0%), 309.27 (21.6%), 310.28 (2.7%)

ETE

Chemical Formula: $C_{20}H_{34}O_2$
Exact Mass: 306.26
Molecular Weight: 306.48
m/z: 306.26 (100.0%), 307.26 (22.1%), 308.26 (2.7%)

Chemical Formula: $C_{20}H_{32}O_2$
Exact Mass: 304.24
Molecular Weight: 304.47
m/z: 304.24 (100.0%), 305.24 (21.7%), 306.25 (2.3%)

ETA

… … … … … … … … … … … … … … US 9,670,126 B2

METHODS OF MAKING 15-HYDROXY FATTY ACID DERIVATIVES

PRIORITY CLAIM

This application claims priority to U.S. Provisional Patent Application Ser. No. 61/896,901, filed Oct. 29, 2013, the entire contents of which are incorporated herein and relied upon.

SUMMARY

The present disclosure provides a two-step process for the production of 15-hydroxy fatty acid derivatives, such as 15-(S)-hydroxyeicosatrienoic acid (HETrE or 15-(S)-HETrE) or 15(S)-hydroxyeicosapentaenoic acid (HEPE or 15(S)-HEPE) starting from the corresponding fatty acid (e.g., dihomo-γ-linolenic acid (DGLA) or eicosapentaenoic acid (EPA), respectively). The first step involves the enzymatic oxidation of the fatty acid to a 15(S)-hydroperoxide fatty acid intermediate (e.g., using a liquid enzyme formulation), followed by reduction to the 15(S)-hydroxy fatty acid derivative. In some embodiments, the enzymatic oxidation step includes contacting the fatty acid with lipoxygenase enzyme, optionally obtained from soy flour. In some embodiments, the step of reducing the 15(S)-hydroperoxy fatty acid intermediate comprises an in-situ reduction with cysteine. In some embodiments, at least a portion of the process is conducted in the exclusion (e.g., partial exclusion) of air. In some embodiments, the process further comprises isolating and/or purifying the 15(S)-hydroxy fatty acid derivative to form a crude active pharmaceutical ingredient (API) grade product. In some embodiments, the isolating and/or purifying step comprises chromatography purification and/or crystallization. In some embodiments, the process is scaled to produce multi-kilogram quantities of the API, optionally conforming to cGMP.

In some embodiments, the fatty acid is DGLA, the 15(S)-hydroperoxy fatty acid intermediate is 15(S)-HPETrE, and the 15(S)-hydroxy fatty acid derivative is 15(S)-HETrE. In other embodiments, the fatty acid is EPA, the 15(S)-hydroperoxy fatty acid intermediate is 15(S)-HPEPE, and the 15(S)-hydroxy fatty acid derivative is 15(S)-HEPE.

BRIEF DESCRIPTION OF THE FIGURES

FIG. 15 shows UPLC purity data for HETrE over 4.5 days of refluxing in a 40% MtBE:cyclohexane mixture (75° C. external temperature).

DETAILED DESCRIPTION

Figure 1:
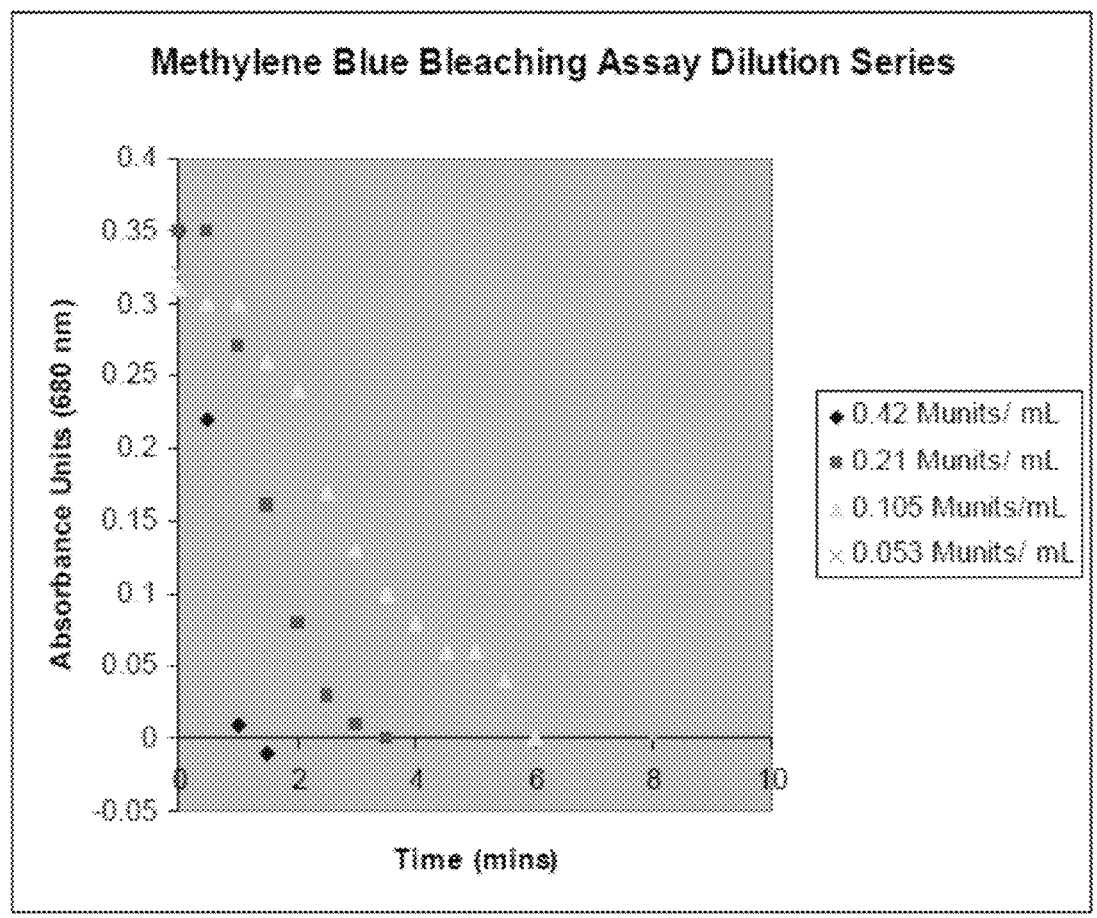
FIG. 1 shows decrease in absorbance of methylene blue solution (680 nm) over time as a function of increasing lipoxygenase enzyme concentration in accordance with one embodiment of the present disclosure.

The present disclosure provides methods of making 15-(S)-hydroxyeicosatrienoic (15-(S)-HETrE) from dihomo-γ-linolenic acid (DGLA). In one step, DGLA is bio-oxidized at the ω6 position, followed by reduction of the resulting hydroperoxide using a reducing agent (e.g., sodium borohydride and/or cysteine). A representative process is shown in Scheme 1. In some embodiments, the 15(S)-HETrE is formed in a single step (e.g., without isolating or purifying the 15(S)-HPETrE intermediate).

Scheme 1

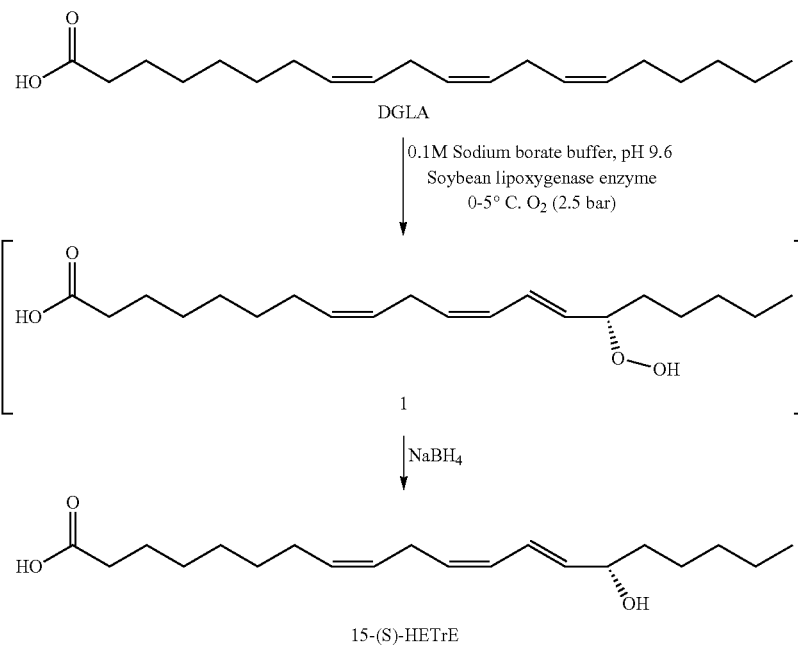

A cost effective enzymatic process for the delivery of kilogram and greater amounts of GMP 15-(S)-HETrE and 15(S)-HEPE is needed (e.g., for use in clinical study programs). In one embodiment, production of 100, 250 and 500 kg batches of GMP 15(S)-HETrE was carried out. The outcome of this program of work was the preparation of 15(S)-HETrE from DGLA, via bio-oxidation with soybean lipoxygenase P1 enzyme to give 15(S)-HPETrE, followed by reduction with 1.1 equivalents of sodium borohydride. After acidification and extractive work-up, the isolated crude 15-(S)-HETrE was purified by column chromatography on silica gel giving a yield of 50% with a purity of >95% by HPLC area percent (235 nm).

It was shown that the bio-oxidation reaction could also be performed using soy flour as a cheaper source of the enzyme; however, downstream processing was not convenient.

In another embodiment, a 500+ g demonstration batch of non-GMP 15(S)-HETrE (e.g., for toxicology studies) was prepared. In this embodiment, 500+ g of 15(S)-HETrE (>95% purity by HPLC area %, 235 nm) was prepared from DGLA. LC-MS and MS-MS analysis of the isolated impurities suggested that there were di-and tri-oxygenated compounds amongst the ~5% impurities present in the final product.

In some embodiments, the method comprises oxidizing DGLA with an oxidant to form 15(S)-HPETrE. In some embodiments, the oxidant is an enzymatic oxidant, such as a lipoxygenase. In some embodiments, the oxidant is soybean lipoxygenase enzyme (e.g., lipoxygenase P1 enzyme). In some embodiments, the soybean lipoxygenase enzyme is purified. In other embodiments, the soybean lipoxygenase enzyme is used as a component of a mixture, for example, soy flour.

The oxidation step may occur in aqueous media, and at a pH suitable to enable enzymatic activity. For example, when the oxidant is soybean lipoxygenase enzyme, the oxidation step may occur in buffered aqueous solvent at basic pH (e.g., pH of about 9, or about 9.6). The oxidant and/or enzyme may be present in a stoichiometric excess compared to the amount of DGLA. For example, the oxidant and/or enzyme may be present in about 1 equivalents, about 1.1 equivalents, about 1.2 equivalents, about 1.3 equivalents, about 1.4 equivalents, about 1.5 equivalents, about 1.6 equivalents, about 1.7 equivalents, about 1.8 equivalents, about 1.9 equivalents, about 2 equivalents, about 2.1 equivalents, about 2.2 equivalents, about 2.3 equivalents, about 2.4 equivalents, about 2.5 equivalents, about 2.6 equivalents, about 2.7 equivalents, about 2.8 equivalents, about 2.9 equivalents, about 3 equivalents, about 3.1 equivalents, about 3.2 equivalents, about 3.3 equivalents, about 3.4 equivalents, about 3.5 equivalents, about 3.6 equivalents, about 3.7 equivalents, about 3.8 equivalents, about 3.9 equivalents, about 4 equivalents, or greater than about 4 equivalents.

In some embodiments, the oxidation step requires addition of an oxygen source, for example when the oxidation step includes contacting the DGLA with an enzyme. In such embodiments, the oxidation step may occur in the presence of an oxygen source, such as atmospheric oxygen or purified (e.g., at least partially purified) gaseous oxygen. In some embodiments, the oxidation step occurs under a pressurized oxygen atmosphere, for example at about 1.1 bar, about 1.2 bar, about 1.3 bar, about 1.4 bar, about 1.5 bar, about 1.6 bar, about 1.7 bar, about 1.8 bar, about 1.9 bar, about 2 bar, about 2.1 bar, about 2.2 bar, about 2.3 bar, about 2.4 bar, about 2.5 bar, about 2.6 bar, about 2.7 bar, about 2.8 bar, about 2.9 bar, about 3 bar, about 3.1 bar, about 3.2 bar, about 3.3 bar, about 3.4 bar, about 3.5 bar, about 3.6 bar, about 3.7 bar, about 3.8 bar, about 3.9 bar, about 4 bar, or greater than about 4 bar.

The temperature of the oxidation step may be controlled to avoid excess heat generation. In some embodiments, for example, the oxidation step may occur at about 0-5° C.

In some embodiments, the oxidation step comprises contacting the DGLA with about 2 equivalents of soybean lipoxygenase P1 enzyme in the presence of aqueous buffer (e.g., 0.1 M sodium borate buffer) at pH about 9.6 under oxygen atmosphere at about 2.5 bar at 0-5° C.

In another embodiment, the oxidation step comprises contacting the DGLA with about 2 equivalents of soybean lipoxygenase enzyme as a crude soy flour extract in the presence of aqueous buffer (e.g., 0.1M sodium borate buffer) at pH about 9.6 in a pressurized oxygen atmosphere at 0-5° C.

In some embodiments, the step of reducing the 15(S)-HPETrE intermediate to form 15(S)-HETrE comprises contacting the 15(S)-HPETrE intermediate with a reducing agent to form the 15(S)-HETrE. In some embodiments, the reducing agent is sodium borohydride. In other embodiments, the reducing agent is cysteine. Cysteine, as a milder reducing agent, offers additional advantages over borohydride-type reducing agents. For example, cysteine does not form hydrogen gas as a byproduct, thus enabling safer scale-up opportunities. In addition, cysteine is a stable reagent and does not require the special handling or storage techniques required for borohydride-type reagents. In addition, the oxidized form of cysteine (cystine) is a stable dipeptide that is only partially soluble in water, which offers convenient purification opportunities over some other reducing agents.

In some embodiments, the step of oxidizing the DGLA and the step of reducing the 15(S)-HPETrE intermediate to form 15(S)-HETrE occur in a single reaction vessel without a step of isolating or purifying the 15(S)-HPETrE intermediate. In such embodiments, the method comprises contacting the DGLA with an oxidant and/or an enzyme, as described above, in the presence of the reducing agent. The reducing agent may be present in a stoichiometric excess amount, for example, about 2 equivalents compared to the amount of DGLA. In some embodiments, the reducing agent is cysteine.

In some embodiments, the method comprises contacting the DGLA with an oxidant and/or an enzyme, as described above, in the presence of the reducing agent. The reducing agent may be initially present in a stoichiometric excess amount, for example, about 2 equivalents compared to the amount of DGLA. The method may further comprise adding an additional amount of the reducing agent, for example about another 1 equivalent, to the reaction vessel after a period of time. In some embodiments, the reducing agent is cysteine.

In some embodiments, the method comprises oxidizing EPA with an oxidant to form 15(S)-HPEPE. In some embodiments, the oxidant is an enzymatic oxidant, such as a lipoxygenase. In some embodiments, the oxidant is soybean lipoxygenase enzyme (e.g., lipoxygenase P1 enzyme). In some embodiments, the soybean lipoxygenase enzyme is purified. In other embodiments, the soybean lipoxygenase enzyme is used as a component of a mixture, for example, soy flour.

In some embodiments, the step of oxidizing the EPA and the step of reducing the 15(S)-HPEPE intermediate to form 15(S)-HEPE occur in a single reaction vessel without a step of isolating or purifying the 15(S)-HPEPE intermediate. In such embodiments, the method comprises contacting the EPA with an oxidant and/or an enzyme, as described above, in the presence of the reducing agent. The reducing agent may be present in a stoichiometric excess amount, for example, about 2 equivalents compared to the amount of EPA. In some embodiments, the reducing agent is cysteine.

In some embodiments, the step of reducing the 15(S)-HPEPE intermediate to form 15(S)-HEPE comprises contacting the 15(S)-HPEPE intermediate with a reducing agent to form the 15(S)-HEPE. In some embodiments, the reducing agent is sodium borohydride. In other embodiments, the reducing agent is cysteine. Cysteine, as a milder reducing agent, offers additional advantages over borohydride-type reducing agents. For example, cysteine does not form hydrogen gas as a byproduct, thus enabling safer scale-up opportunities. In addition, cysteine is a stable reagent and does not require the special handling or storage techniques required for borohydride-type reagents. In addition, the oxidized form of cysteine (cystine) is a stable dipeptide that is only partially soluble in water, which offers convenient purification opportunities over some other reducing agents.

In some embodiments, the method comprises contacting the EPA with an oxidant and/or an enzyme, as described above, in the presence of the reducing agent. The reducing agent may be initially present in a stoichiometric excess amount, for example, about 2 equivalents compared to the amount of EPA. The method may further comprise adding an additional amount of the reducing agent, for example about another 1 equivalent, to the reaction vessel after a period of time. In some embodiments, the reducing agent is cysteine.

In some embodiments, the 15(S)-HEPE is converted to an ester (e.g., an ethyl ester) by treating the 15(S)-HEPE with alkyl bromide (e.g., ethyl bromide) and potassium carbonate in dry acetone. The crude ester formed in such embodiments may be conveniently purified by treatment with charcoal and silica gel to form high purity 15(S)-HEPE.

In some embodiments, the method provides compositions comprising a 15-hydroxy fatty acid derivative and one or more impurities. In some embodiments, the one or more impurities consist of, essentially consist of, or comprise an over-oxidation product, an over-reduced product, a dimer, and/or a positional isomer of the 15(S)-hydroxy fatty acid derivative. In some embodiments, the over-oxidation product is a di-hydroxylated compound, a compound having one or more extra $C=C$ double bonds, or a combination thereof. In some embodiments, the over-reduced product is a compound having one or more fewer $C=C$ double bonds than the described 15(S)-hydroxy fatty acid derivative. In some embodiments, the dimer is an ester-dimer formed between a carboxylic acid moiety of a first molecule and a hydroxy moiety of a second molecule.

In some embodiments, the present disclosure provides compositions comprising a 15(S)-hydroxy fatty acid derivative. In some embodiments, the composition further comprises one or more impurities. In some such embodiments, the 15(S)-hydroxy fatty acid derivative is present in an amount of at least about 90%, by weight of all fatty acids present in the composition, for example at least about 90%, at least about 91%, at least about 92%, at least about 93%, at least about 94%, at least about 95%, at least about 96%, at least about 97%, at least about 98%, or at least about 99%, by weight of all fatty acids present in the composition. In some embodiments, the 15(S)-hydroxy fatty acid derivative is in the form of an ester, such as an ethyl ester. In some embodiments, the composition further comprises an impurity, wherein the impurity is present in an amount of no more than about 10%, by weight of all fatty acids present, for example no more than about 10%, no more than about 9%, no more than about 8%, no more than about 7%, no more than about 6%, no more than about 5%, no more than about 4%, no more than about 3%, no more than about 2%, no more than about 1%, of all fatty acids present in the composition.

In some embodiments, the present disclosure provides compositions comprising 15(S)-HETrE. In some embodiments, the composition further comprises one or more impurities. In some such embodiments, the 15(S)-HETrE is present in an amount of at least about 90%, by weight of all fatty acids present in the composition, for example at least about 90%, at least about 91%, at least about 92%, at least about 93%, at least about 94%, at least about 95%, at least about 96%, at least about 97%, at least about 98%, or at least about 99%, by weight of all fatty acids present in the composition. In some embodiments, the 15(S)-HETrE is in the form of an ester, such as an ethyl ester. In some embodiments, the composition further comprises an impurity, wherein the impurity is present in an amount of no more than about 10%, by weight of all fatty acids present, for example no more than about 10%, no more than about 9%, no more than about 8%, no more than about 7%, no more than about 6%, no more than about 5%, no more than about 4%, no more than about 3%, no more than about 2%, no more than about 1%, of all fatty acids present in the composition.

In some embodiments, the present disclosure provides compositions comprising 15(S)-HEPE. In some embodiments, the composition further comprises one or more impurities. In some such embodiments, the 15(S)-HEPE is present in an amount of at least about 90%, by weight of all fatty acids present in the composition, for example at least about 90%, at least about 91%, at least about 92%, at least about 93%, at least about 94%, at least about 95%, at least about 96%, at least about 97%, at least about 98%, or at least about 99%, by weight of all fatty acids present in the composition. In some embodiments, the 15(S)-HEPE is in the form of an ester, such as an ethyl ester. In some embodiments, the composition further comprises an impurity, wherein the impurity is present in an amount of no more than about 10%, by weight of all fatty acids present, for example no more than about 10%, no more than about 9%, no more than about 8%, no more than about 7%, no more than about 6%, no more than about 5%, no more than about 4%, no more than about 3%, no more than about 2%, no more than about 1%, of all fatty acids present in the composition.

EXAMPLES

Example 1

Colorimetric Assay for Assessing Lipoxygenase Activity of Crude Vegetable Homogenates Linoleic hydroperoxide, 3-methyl-2-benzothiazoline (MBTH), and 3-(dimethylamino)benzoic acid (DMAB) are known to react in the presence of haemoglobin to give a purple indamine dye, absorbing at 590 nm. The absorbance at this wavelength is linear with the concentration of linoleic hydroperoxide up to 35 uM.

1 g soy flour was extracted into 10 mL of the appropriate pH adjusted buffer or water (1:10 w/v) over a period of up to 24 hours, at either 4° C. or a mbient temperature. The reactions were carried out in a test tube with magnetic stirring (~500 rpm). For the 1 and 2 hour time points, the extraction solutions were allowed to settle for ~10 minutes before 10 µL of the enzyme solution was withdrawn and added to assay solution A (containing linoleic acid and DMAB) (1 mL), in a 4 mL cuvette. After incubating for ~5 minutes at room temperature, assay solution B (MBTH and haemoglobin) (1 mL) was added and further incubated for ~5 minutes before recording the absorbance reading (Table 1). A blue colour formation was observed in all samples, except the sodium borate, pH 10.4 extract samples and blank (all reagents, except enzyme). A slight grey colour was observed in this case with an absorbance of ~0.2. A blank was run with all reagents and enzyme except linoleic acid, giving an absorbance of 0.2. It was determined that the enzyme solution was interfering with the absorbance reading.

TABLE 1

Absorbance readings at 590 nm for flour extracts under various conditions

| Buffer, initial pH | Final extract pH | Temperature (° C.) | Absorbance (590 nm) at Time point (hrs) | | | | | | | |
|---|---|---|---|---|---|---|---|---|---|---|
| | | | 1 hrs | | 2 hrs | | 5 hrs | | 24 hrs | |
| Sodium acetate, pH 10 | 6.8 | 4 | 0.50 | 0.36 | 0.43 | 0.39 | 0.25 | 0.20 | 0.23 | 0.30 |
| | | ambient | 0.43 | 0.31 | 0.48 | 0.44 | 0.26 | 0.18 | 0.31 | 0.27 |

TABLE 1-continued

Absorbance readings at 590 nm for flour extracts under various conditions

| Buffer, initial pH | Final extract pH | Temperature (° C.) | Absorbance (590 nm) at Time point (hrs) | | | | | | | |
|---|---|---|---|---|---|---|---|---|---|---|
| | | | 1 hrs | | 2 hrs | | 5 hrs | | 24 hrs | |
| Sodium acetate, pH 4.5 | 5.2 | 4 | 0.43 | 0.45 | 0.53 | 0.53 | 0.29 | 0.29 | 0.37 | 0.31 |
| | | ambient | 0.52 | 0.46 | 0.54 | 0.51 | 0.25 | 0.26 | 0.40 | 0.35 |
| Sodium borate, pH 10.4 | 10.1 | 4 | 0.20 | 0.21 | 0.21 | 0.16 | 0.06 | 0.02 | 0.00 | 0.04 |
| | | ambient | 0.20 | 0.20 | 0.23 | 0.20 | 0.0 | 0.0 | 0.05 | 0.22 |
| Sodium borate, pH 4.5 | 6.1 | 4 | 0.52 | 0.49 | 0.62 | 0.54 | 0.37 | 0.24 | 0.33 | 0.31 |
| | | ambient | 0.41 | 0.44 | 0.62 | 0.54 | 0.24 | 0.34 | 0.36 | 0.53 |
| Water, pH 7 | 6.8 | 4 | 0.41 | 0.41 | 0.38 | 0.41 | 0.20 | 0.24 | 0.23 | 0.29 |
| | | ambient | 0.30 | 0.31 | 0.47 | 0.48 | 0.19 | 0.18 | 0.25 | 0.27 |

The remaining time points (5 and 24 hours) were analysed differently. Extraction solutions were allowed to settle for ~10 minutes before 10 μL of the enzyme solution was withdrawn and added to assay solution A (containing linoleic acid and DMAB) (0.5 mL), in a 2 mL eppendorf tube. After incubating for ~5 minutes at room temperature, assay solution B (MBTH and haemoglobin) (0.5 mL) was added and further incubated for ~5 minutes. Sodium lauryl sulphate solution (1% w/v) (0.5 mL) was added to quench the reaction and the solutions were centrifuged at 9.8 rcf, 4° C. for 5 minutes. The solution was then decanted into a 4 mL cuvette and analysed as before. The results did not show any particular trend.

Example 2

Alternative Colorimetric Assay Conditions

To test the assay sensitivity, a dilution series was set-up using the freeze dried enzyme at the original loading value (0.42 Munits (4.11 mg)/mL based on supplier certificate of analysis) and diluting by half until no more colorimetric detection was observed. This was also analysed with the methylene blue bleaching method (Suda et al., J. Agric. Food Chem. 43, 3, 1995, p. 742, EP no. 2118126 A1) whereby the decrease in absorbance of a 100 μM methylene blue solution was analysed at 680 nm, over time when incubated with the enzyme solution in the presence of linoleic acid. The methylene blue bleaching assay was conducted using 2.1 mL of 0.2 M Tris-HCl buffer, pH 9.0, 0.3 mL 100 μM methylene blue solution, 0.3 mL 10 mM sodium lineoleate substrate and 0.3 mL soyflour extract (total volume 3 mL).

TABLE 2

Absorbance readings at 680 nm for purified enzyme dilution series (methylene blue bleaching method)

| Enzyme Loading (Munits/mL) | Absorbance (680 nm) at Time point t (mins) | | | | | | | | | | |
|---|---|---|---|---|---|---|---|---|---|---|---|
| | t = 0 | t = 1 | t = 2 | t = 3 | t = 4 | t = 5 | t = 6 | t = 7 | t = 8 | t = 9 | t = 10 |
| 0.420 | 0.34 | 0.00 | — | — | — | — | — | — | — | — | — |
| 0.210 | 0.27 | 0.03 | — | — | — | — | — | — | — | — | — |
| 0.105 | 0.33 | 0.03 | 0.01 | — | — | — | — | — | — | — | — |
| 0.053 | 0.31 | 0.25 | 0.08 | 0.00 | — | — | — | — | — | — | — |
| 0.026 | 0.28 | 0.23 | 0.19 | 0.10 | 0.08 | 0.05 | 0.00 | | | | |
| 0.013 | 0.35 | 0.32 | 0.32 | 0.32 | 0.22 | 0.22 | 0.16 | 0.14 | 0.11 | 0.09 | 0.08 |
| 0.007 | 0.29 | 0.27 | 0.26 | 0.27 | 0.26 | 0.26 | 0.27 | 0.26 | 0.26 | 0.28 | 0.26 |

For the DMAB-MBTH assay, 10 μL of the enzyme solution was withdrawn and added to assay solution A (containing linoleic acid and DMAB) (0.5 mL), in a 2 mL eppendorf. After incubating for ~5 minutes at room temperature, assay solution B (MBTH and haemoglobin) (0.5 mL) was added and further incubated for ~5 minutes. Sodium lauryl sulphate solution (1% w/v) (0.5 mL) was added to quench the reaction and the solutions were centrifuged at 16.1 rcf, 4° C. for 10 minutes. The solution was then decanted into a 4 mL cuvette and analysed as before. This was performed in duplicate.

TABLE 3

Absorbance readings for purified enzyme dilution series at 590 nm (DMAB-MBTH assay)

| Enzyme Loading (Munits/mL) | Absorbance (590 nm) | |
|---|---|---|
| | 1 | 2 |
| 0.420 | 0.17 | 0.19 |
| 0.210 | 0.21 | 0.18 |
| 0.105 | 0.23 | 0.27 |
| 0.053 | 0.22 | 0.22 |
| 0.026 | 0.26 | 0.20 |

TABLE 3-continued

Absorbance readings for purified enzyme dilution series at 590 nm (DMAB-MBTH assay)

| Enzyme Loading | Absorbance (590 nm) | |
|---|---|---|
| (Munits/mL) | 1 | 2 |
| 0.013 | 0.06 | 0.08 |
| 0.007 | 0.00 | 0.03 |

From the results in Table 3, it appeared that the absorbance readings obtained using this method, did not correspond in a linear fashion with the concentration of the enzyme in the solution. The original method was used for the assay of crude vegetable lipoxygenases at pH 6. It is reported that haemoglobin exhibits quasi-lipoxygenase activity at an optimum pH of 8.5 and linoleic acid concentration of 0.5 mM. As the assay was being conducted at pH 9, this may have had some bearing on the results obtained. It was noted however, that no colour formation was observed in a blank containing all the reagents except the enzyme. However, on the basis of the results obtained it was decided to proceed with the methylene blue bleaching method. The method is simple and rapid, although not particularly sensitive and it is difficult to quantify. The activity levels are determined by the time taken for the colour to disappear (i.e. absorbance at 680 nm to reach 0). In order to distinguish between higher enzyme loadings, the dilution series with purified enzyme was repeated using a lower concentration of the enzyme solution. Only 30 μL of enzyme solution was added to the methylene blue bleaching solution and the volume was made up to 3 mL with 270 μL of distilled water. The results obtained are recorded in Table 4.

TABLE 4

Absorbance readings at 680 nm for purified enzyme dilution series using lower enzyme concentration (methylene blue bleaching method)

| Enzyme Load | Absorbance at Time t (mins) | | | | | | | | |
|---|---|---|---|---|---|---|---|---|---|
| (Munit/mL) | t = 0 | t = 0.5 | t = 1 | t = 1.5 | t = 2.0 | t = 2.5 | t = 3.0 | t = 3.5 | t = 4.0 |
| 0.420 | 0.35 | 0.22 | 0.01 | −0.01 | — | — | — | — | — |
| 0.210 | 0.35 | 0.35 | 0.27 | 0.16 | 0.08 | 0.03 | 0.01 | 0.00 | — |
| 0.105 | 0.31 | 0.30 | 0.30 | 0.26 | 0.24 | 0.17 | 0.13 | 0.10 | 0.08 |
| 0.053 | 0.32 | — | 0.31 | — | 0.31 | — | 0.25 | — | 0.18 |

| Enzyme Load | Absorbance at Time t (mins) | | | | | | | | |
|---|---|---|---|---|---|---|---|---|---|
| (Munit/mL) | t = 4.5 | t = 5.0 | t = 5.5 | t = 6.0 | t = 6.5 | t = 7.0 | t = 7.5 | t = 8.0 | t = 8.5 |
| 0.420 | — | — | — | — | — | — | — | — | — |
| 0.210 | — | — | — | — | — | — | — | — | — |
| 0.105 | 0.06 | 0.06 | 0.04 | 0.00 | — | — | — | — | — |
| 0.053 | — | 0.16 | — | 0.06 | — | 0.05 | 0.02 | 0.00 | 0.01 |

A graphical representation of the dilution series is shown in FIG. 1. An induction time, (0.5-2 mins) for the absorbance to begin to decrease, is observed for samples with a lower enzyme concentration.

It was determined that the activity of a soyflour extract could be assayed colorimetrically using this method against a solution of the commercial enzyme, giving an indication of sufficient activity to perform the required oxidation reaction.

Example 3

Cysteine as Reducing Agent

Figure 2:
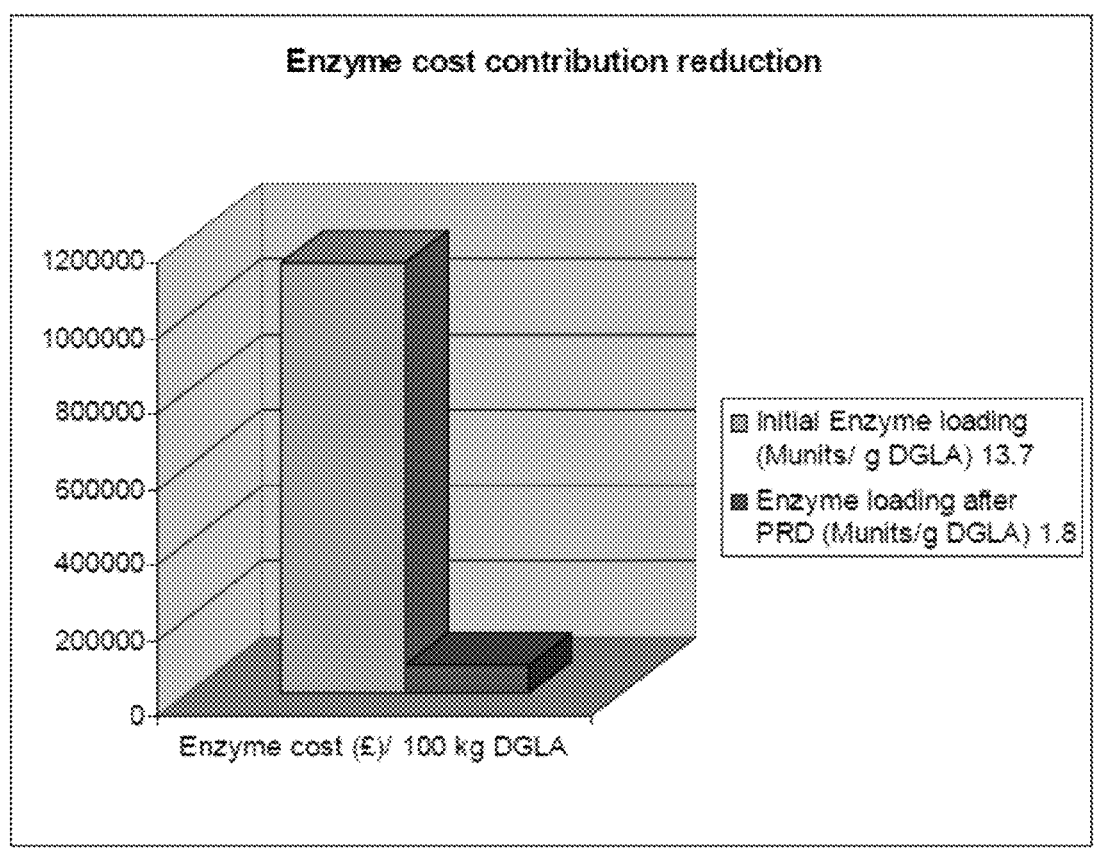
FIG. 2 shows enzyme cost contribution reduction due to reduced enzyme loadings and cheaper enzyme source in accordance with one embodiment of the present disclosure.

An alternative supply of freeze dried enzyme was sourced. Initial trials showed that enzyme loading could be reduced by up to half. In combination with the alternative reducing agent (cysteine), enzyme loadings were reduced from initial 13.7 Munits per gram of DGLA substrate (liquid enzyme preparation) to 1.8 Munits per gram (freeze dried enzyme). A cost reduction, for lipoxygenase enzyme, from £11.37 per gram DGLA to £0.75 per gram DGLA (~15 fold reduction, FIG. 2) was realised. This was due to two factors: decreased enzyme loading and cheaper supply (£0.42/Munit for freeze dried enzyme vs £0.83/Munit for liquid enzyme preparation).

It was also observed that the freeze dried enzyme supplied had good stability. Although recommended to be stored at −20° C., and desiccated after use, the batch was stored at ambient, atmospheric conditions for two weeks before being utilised in a reaction using the optimised enzyme loadings (1.8 Munits/g DGLA). No deterioration in performance was observed. The reaction was carried out in buffer solution to maintain pH and solubilise reaction components. Cysteine, a mild reducing agent, was used in place of sodium borohydride. Use of cysteine enabled the oxidation/reduction reaction to be carried out in one step. In addition no flammable hydrogen was generated during reaction/quench. Furthermore, fewer over-oxidation products were produced, likely due to cysteine's anti-oxidant properties. It is also believed that the addition of the reducing agent at beginning of the process helps to lessen irreversible enzyme inactivation by high concentrations of hydroperoxide, thus leading to lower enzyme requirement (e.g., cost savings) and lower potential for over-oxidation.

Example 4

Enzyme Loading

Previous bio-oxidation reactions were conducted using a liquid enzyme preparation with an enzyme loading of ~13.7

Munits of activity per gram of DGLA substrate (1 unit defined as the enzyme causing an increase of 0.001 AU per minute at 234 nm when incubated with 0.02% lineolate at 25° C. in 0.1M borate buffer, pH 9.0, in a total volume of 1.0 mL). An alternative supply of lipoxygenase as a freeze dried powder was also tested. The bio-oxidation reaction was repeated with the freeze dried enzyme using ~13.7 Munits of activity per gram of DGLA substrate and a similar reaction completion profile by $^1$H NMR spectroscopy was obtained. This reaction was repeated a further 3 times, decreasing the enzyme loading by half each time. The results are summarised in Table 5.

TABLE 5

Results of initial enzyme loading study using freeze-dried pure enzyme

| Experiment No. | Enzyme loading Munits/g DGLA substrate | Reaction completion as judged by $^1$H NMR |
|---|---|---|
| 1822-159 | ~13.7 | Complete |
| 1822-161 | ~6.87 | Complete |
| 1822-175 | ~3.4 | Inconclusive due to overlapping signals. DGLA remaining. Confirmed by TLC. |
| 1822-177 | ~5.2 | Inconclusive due to overlapping signals. DGLA remaining. Confirmed by TLC. |

The results of these trials show that the enzyme loading could be reduced by at least half with reaction completion still being obtained within 1 hour. Although the $^1$H NMR spectra obtained for the lower loading samples were inconclusive, DGLA was still visible by NMR, and its presence was confirmed by TLC.

Example 5

Enzyme Source

Previous reactions were performed using a liquid preparation of lipoxygenase, giving reaction completion at a loading of 13.7 Munits per gram of DGLA. An alternative supply of freeze-dried pure enzyme was obtained and reaction completion reached using an enzyme loading of only 6.87 Munits per gram of DGLA.

Example 6

Reaction Medium

An experiment was conducted using pure water instead of buffer. DGLA was added to the water giving two immiscible layers. The pH was adjusted to 9.8 with 2M sodium hydroxide and stirred to give an emulsion. Freeze-dried enzyme (6.87 Munits per gram of DGLA) was added and the reaction conducted as before. After 1 hour the reaction mixture was still a cloudy emulsion, indicative of incomplete conversion. $^1$H NMR spectroscopy showed approximately 45% unreacted DGLA and some of the over oxidised impurity. This suggests that buffer is required to maintain the requisite pH (~9) and help solubilise the substrate. It is believed that 15-(S)-HPETrE also helps to solubilise the DGLA substrate.

Example 7

Reducing Agent

The intermediate hydroperoxide was previously reduced cleanly, in one pot sequence, using 1.1 equivalents of sodium borohydride. However, this leads to the production of hydrogen gas, especially during work-up and required a large volume of 10% citric acid solution for pH adjustment. In scale up, sodium borohydride is disfavored because of the hydrogen issue, charging mode, and projected long quench time (~17 hrs) on plant.

Experiments were conducted where cysteine was used as the reducing agent instead of sodium borohydride. A number of reactions were performed using various enzyme loadings. The various permutations are detailed in Table 6. The reactions were carried out in a Parr reactor, under oxygen pressure (2.5 bar).

Two equivalents of cysteine appear to be required initially. Addition of 3 equivalents caused the reaction to stall, or at least progress very slowly, likely due to the rapid removal of the enzyme activating hydroperoxide. However, if two equivalents of cysteine are used initially, a further equivalent of cysteine is required to be added to reduce hydroperoxide remaining after one hour reaction time. This is probably due to the oxidation of cysteine in the reaction mixture by oxygen, rather than the hydroperoxide. It was also found that reduction of the enzyme loading to as low as 1.8 Munits activity per gram of DGLA was achievable under these conditions, giving virtually complete consumption of DGLA within a few hours and reduced impurity (e.g., over-oxidised products) formation.

TABLE 6

Results of reactions using cysteine reducing agent and varied enzyme loading (freeze-dried enzyme)

| Experiment Number | Point of Substrate Addition | Point of Enzyme Addition | Point of Cysteine Addition | Results |
|---|---|---|---|---|
| 1822-193 | All added at beginning | All added at beginning (~14 Munits/g DGLA) | Added after 60 mins (2 eq.). | After 1 hour stirring with cysteine under O2, mixture of HPETrE, HETrE and overoxidised impurities. |
| 1822-195 | All added at beginning | All added at beginning (~14 Munits/g DGLA) | All added at beginning (2 eq.) | After 30 mins under O2, mixture of HPETrE and HETrE by 1H NMR. Further stirring at atmospheric showed no further conversion. After standing overnight (4° C.), NMR showed little further change. |
| 1822-197 | All added at beginning | All added at beginning (~14 Munits/g DGLA) | All added at beginning (3 eq.) | After 30 mins under O2 plus 15 mins settling, mixture of HETrE and DGLA, no HPETrE by 1H NMR. After standing overnight (4° C.) at atmospheric, further DGLA conversion was observed |

TABLE 6-continued

Results of reactions using cysteine reducing agent and varied enzyme loading (freeze-dried enzyme)

| Experiment Number | Point of Substrate Addition | Point of Enzyme Addition | Point of Cysteine Addition | Results |
|---|---|---|---|---|
| 1822-199 | All added at beginning | All added at beginning (~7 Munits/g DGLA) | 2 eq. added at beginning plus further 1 eq. after 60 mins. | After 60 mins under O2, mixture of HETrE and small amount of HPETrE by 1H NMR. Added further 1 equivalent cysteine and stirred for 60 mins under atmospheric. No HPETrE, some residual DGLA by 1H NMR. HPLC area % purity (235 nm) 96.8%. Recovered 77% crude HETrE and purified by column chromatography to give 45% yield of clear, pale yellow oil (96.7% area by HPLC). Total recovery from column including crude fractions 71%. |
| 1891-001 | All added at beginning | All added at beginning (~3.5 Munits/g DGLA) | 2 eq. added at beginning plus further 1 eq. after 60 mins. | After 60 mins under 02, mixture of HETrE small amount of HPETrE and DGLA by 1H NMR. Added further 1 equivalent cysteine and stirred for 60 mins under atmospheric. No HPETrE, some residual DGLA by 1H NMR. Filtered through Celite to remove precipitated cystine and adjusted pH to 3 with solid citric acid. Stored at 4° C. overnight. Extracted with MTBE to yield 76% crude HETrE. HPLC area % purity (252 nm) 93.55%. |
| 1891-003 | All added at beginning | All added at beginning (~1.8 Munits/g DGLA) | 2 eq. added at beginning plus further 1 eq. after 60 mins. | After 60 mins under O2, mixture of HETrE small amount of HPETrE and DGLA (~10 wt %) by 1H NMR. Added further 1 equivalent cysteine and stirred for 60 mins under O2 pressure. No HPETrE, residual DGLA (~6.5 wt %) by 1H NMR. After standing at atmospheric, filtered through Celite to remove precipitated cystine and adjusted pH to 3 with solid citric acid. Extracted with MTBE to yield 70% crude HETrE. No HPETrE, residual DGLA (~1 wt %) by 1H NMR. HPLC area % purity (252 nm) 93.19%. |
| 1891-005 | All added at beginning | All added at beginning (~0.96 Munits/g DGLA) | 2 eq. added at beginning plus further 1 eq. after 60 mins. | After 60 mins under O2, mixture of HETrE small amount of HPETrE and significant DGLA (41 wt %) by 1H NMR. Added further 1 equivalent cysteine and stirred for 60 mins under O2 pressure. No HPETrE, residual DGLA (14 wt %) by 1H NMR. Stirred overnight under O2 pressure. Small amount of HPETrE, residual DGLA (3.5 wt %) by 1H NMR. Added a further 0.25 eq of cysteine and Stirred under O2 pressure for 1 hour. No HPETrE, residual DGLA (3.5 wt %) by 1H NMR. |
| 1891-011 | All added at beginning | All added at beginning (~1.8 Munits/g DGLA) | 2 eq. added at beginning plus further 1 eq. after 60 mins. | After 60 mins under compressed air, mainly DGLA by 1H NMR. Reaction continued overnight under compressed air. 1H NMR HETrE, HPETrE, significant DGLA and impurities. |
| 1891-015 | All added at beginning | All added at beginning (~1.8 Munits/g DGLA) | 2 eq. added after 7 hours | After 60 mins under compressed air, mainly DGLA by 1H NMR. Reaction continued for 6 hours under compressed air. 1H NMR showed ~45% HPETrE, 55% DGLA. Added 2 eq. of cysteine and re-adjusted pH, then stirred overnight. 1H NMR showed ~45% HETrE, 55% DGLA. No further conversion. |

Example 8

Double Batch Fed Fermentor Reaction

A 1 L final volume reaction was carried out in a 3 L fermentor, where the substrate (40 g) and enzyme (1.8 Munits/g DGLA) were added at a constant rate (1.6 mL/min and 2 mL/min) respectively to pH 9.5, 0.1 M sodium borate buffer (850 mL). Oxygen was bubbled through the buffer solution, which was stirred at 500 rpm. The enzyme was added as a solution in pH 4.5, 0.1M sodium acetate solution (150 mL) and the pH of the reaction was maintained at ~9.5 by addition of 3M NaOH (aq). Upon addition of DGLA, significant foaming occurred and some material was expelled from the vessel (~10%). Polypropylene glycol 2000 (20 mL 1:1 v/v with borate buffer) was added as an anti foaming agent, but had little effect. A further 20 mL did not noticeably reduce foaming. Reducing the oxygen flow to the lowest possible setting eventually reduced the foam. An aliquot was analysed by $^1$H NMR after 1.5 hours, which showed residual DGLA (6.25% wt). The reaction was continued for a further 5 hours. The suspension was then filtered through Celite to remove cystine and the clear filtrate was acidified to pH 3 with solid citric acid. The resulting suspension was stored at 4° C. over the weekend. The precipitated product and further cystine residues had settled from the aqueous solution. These were collected by filtration giving a white cream. TLC showed the absence of product in the aqueous filtrate. The collected 'cream' was slurried in MTBE and filtered to leave a granular white solid. The filtrate was concentrated on the rotary evaporator to leave 44 g of yellow oil. $^1$H NMR analysis showed no HPETrE and less than 1%wt residual DGLA. However, the product also contained PPG2000. The oil was slurried in 20% MTBE: hexane (100 mL) and applied to a silica pad (400 g). The pad was eluted with hexane (1.2 L), 20% MTBE: hexane (2 L), and 40% MTBE: hexane (4 L). The product containing fractions were identified by TLC. The initial product containing fractions contained a faint trace of DGLA by TLC; these were combined and concentrated separately to give 13 g of product as a clear, pale yellow oil. $^1$H NMR (CDCl$_3$) ~0.5% DGLA, HETrE. The remaining product containing fractions were combined to give 14 g of product. $^1$H NMR (CDCl$_3$)—HETrE. HPLC area% purity (252 nm)—96.92%. Total recovery of product after column chromatography was 62%. However, significant loses occurred due to the foaming issue in the reactor. This has shown that the reaction does not require to be conducted under pressure if sufficient oxygen is transferred into the mixture via agitation and an extended reaction time did not lead to an increase in side products. Without wishing to be bound by theory, it is believed that this is due to a number of reasons—lower enzyme loading, lower oxygen availability, and reduced amount of the unstable hydroperoxide in the reaction mixture. However, the reaction under a slight oxygen pressure would help to control the problem of reaction foaming.

Example 9

Soyflour as Enzyme Source

Conditions were developed for the extraction of sufficient lipoxygenase activity from 10 g of soyflour to cleanly convert 3 g of DGLA to HETrE (1:10 w/v 0.1 M sodium acetate buffer, pH 4.5, 3 hours, 180 rpm).

Figure 3:
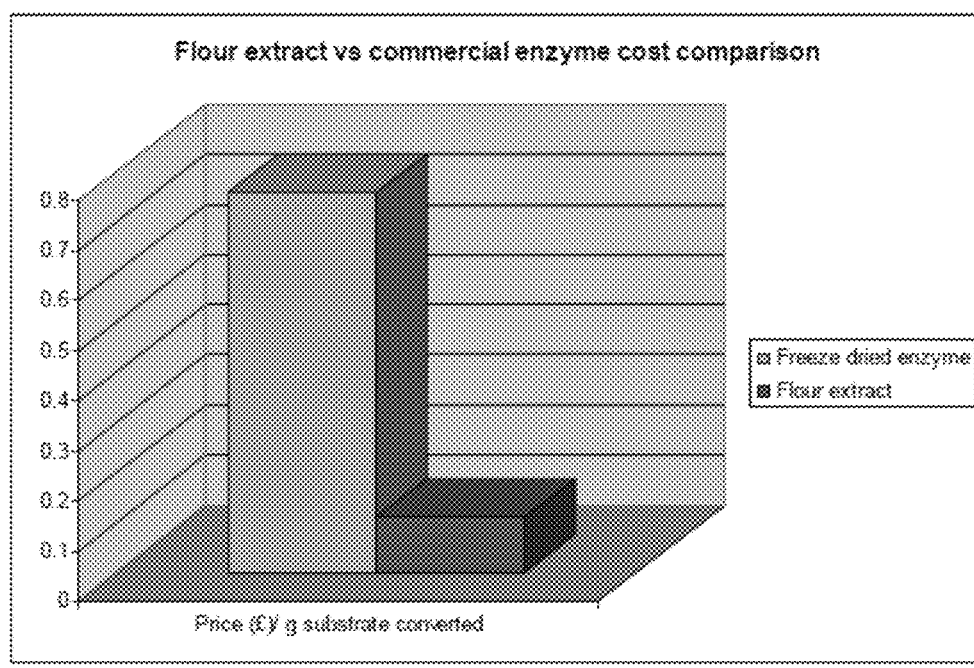
FIG. 3 shows the material cost comparison of commercial freeze-dried enzyme and soyflour extract.

Cost comparison based on current prices of freeze-dried enzyme and soyflour show 7-fold saving on material costs (FIG. 3), however extra unit operation (extraction, filtration) is required on plant scale so potential saving at low volumes is negligible.

Bio-oxidation reactions using soy flour as the enzyme source, carried out under oxygen pressure gave reasonable conversions of DGLA to HPETrE (~95%). Reactions could be performed by adding soy flour directly; however, this produced a viscous reaction mixture. Acidification of the reaction mixture causes precipitation of proteins, which when extracted produced thick emulsions which were difficult to filter. It was found that clean separation of the layers could be achieved with centrifugation, although this would not be feasible on a large scale, due to the volumes involved. There would also be an issue with reactor cleaning, as the flour residues were quite hard to remove.

The active enzyme was instead extracted from the flour into buffer solution at room temperature. After centrifugation, the resulting turbid solution was used to perform the bio-oxidation. This removes the insoluble carbohydrates from the reaction mixture, but emulsions are formed during the work-up procedure due to the presence of significant amounts of proteins.

Isolation of semi-purified enzyme from soy flour was attempted, although this was found to be inactive.

Systematic determination of the optimum conditions for extraction of enzyme activity from defatted soy-flour (buffer medium, pH, time, temperature).

An investigation into extracting enzyme from soy flour considered at pH and extraction buffer (1:10 w/v soy flour loading) (Table 7), and was conducted in parallel with the colorimetric assay investigations.

TABLE 7

Initial lipoxygenase extraction conditions (buffer, pH, temperature)

| Buffer, initial pH | Final extract pH | Temperature (° C.) |
|---|---|---|
| Sodium acetate, pH 10 | 6.8 | 4 ambient |
| Sodium acetate, pH 4.5 | 5.2 | 4 ambient |
| Sodium borate, pH 10.4 | 10.1 | 4 ambient |
| Sodium borate, pH 4.5 | 6.1 | 4 ambient |
| Water, pH 7 | 6.8 | 4 ambient |

The pH of these extract solutions was analysed and it was found that the sodium borate buffer at pH 4.5 had a pH of 6.1 with soy flour added. Sodium acetate buffer, pH 10 had a pH of 6.8 with soy flour added and the pH of a pure water extract was also 6.8. This corresponds with the pH buffering range of the borate (8-10) and acetate (3.6-5.6) buffers. Sodium acetate buffer, pH 4.5 was shifted to pH 5.2 with soy flour added.

Proteins can be damaged by friction like that caused by magnetic agitators. The next set of extractions was carried out in 50 mL centrifuge tubes in temperature controlled orbital shakers. A number of reactions were set-up at various pH and temperatures, and analysed at 3 time points; 1, 2 and 14 hours and 3 temperatures 5, 25 and 40° C. The assay results (determined by methylene blue bleaching at the less discriminating conditions (300 μL enzyme solution)) are shown in Table 8.

TABLE 8

Absorbance readings at 680 nm for soyflour extracts after 1 hour

| Buffer, initial pH | Temperature (° C.) | Absorbance (680 nm) at time point t (mins) | | | | | | |
|---|---|---|---|---|---|---|---|---|
| | | t = 0 | t = 1 | t = 2 | t = 3 | t = 4 | t = 5 | t = 6 |
| Sodium acetate, pH 4.5 | 5 | 0.32 | 0.06 | — | — | — | — | — |
| | 25 | 0.28 | 0.01 | — | — | — | — | — |
| | 40 | 0.30 | 0.02 | — | — | — | — | — |
| Sodium borate, pH 9.0 | 5 | 0.26 | −0.01 | — | — | — | — | — |
| | 25 | 0.27 | 0.01 | 0.00 | — | — | — | — |
| | 40 | 0.28 | 0.04 | 0.01 | — | — | — | — |
| Potassium phosphate monobasic pH 6.5 | 5 | 0.34 | 0.06 | — | — | — | — | — |
| | 25 | 0.27 | −0.01 | — | — | — | — | — |
| | 40 | 0.25 | −0.03 | — | — | — | — | — |

TABLE 9

Absorbance readings at 680 nm for soyflour extracts after 2 hours

| Buffer, initial pH | Temperature (° C.) | Absorbance (680 nm) at time point t (mins) | | | | | | |
|---|---|---|---|---|---|---|---|---|
| | | t = 0 | t = 1 | t = 2 | t = 3 | t = 4 | t = 5 | t = 6 |
| Sodium acetate, pH 4.5 | 5 | 0.23 | 0.01 | — | — | — | — | — |
| | 25 | 0.26 | 0.02 | — | — | — | — | — |
| | 40 | 0.21 | −0.02 | — | — | — | — | — |
| Sodium borate, pH 9.0 | 5 | 0.26 | 0.02 | — | — | — | — | — |
| | 25 | 0.27 | 0.07 | 0.02 | — | — | — | — |
| | 40 | 0.23 | 0.19 | 0.10 | 0.06 | 0.04 | 0.03 | 0.02 |

TABLE 9-continued

Absorbance readings at 680 nm for soyflour extracts after 2 hours

| Buffer, initial pH | Temperature (° C.) | Absorbance (680 nm) at time point t (mins) | | | | | | |
|---|---|---|---|---|---|---|---|---|
| | | t = 0 | t = 1 | t = 2 | t = 3 | t = 4 | t = 5 | t = 6 |
| Potassium phosphate monobasic pH 6.5 | 5 | 0.34 | −0.01 | — | — | — | — | — |
| | 25 | 0.32 | 0.08 | — | — | — | — | — |
| | 40 | 0.27 | 0.03 | — | — | — | — | — |

TABLE 10

Absorbance readings at 680 nm for soyflour extracts after 14 hours

| Buffer, initial pH | Temperature (° C.) | Absorbance (680 nm) at time point t (mins) | | | | | | |
|---|---|---|---|---|---|---|---|---|
| | | t = 0 | t = 1 | t = 2 | t = 3 | t = 4 | t = 5 | t = 6 |
| Sodium acetate, pH 4.5 | 5 | 0.34 | 0.06 | — | — | — | — | — |
| | 25 | 0.33 | 0.04 | — | — | — | — | — |
| | 40 | 0.30 | −0.01 | — | — | — | — | — |
| Sodium borate, pH 9.0 | 5 | 0.30 | 0.01 | 0.01 | — | — | — | — |
| | 25 | 0.33 | 0.22 | 0.11 | 0.06 | 0.03 | — | — |
| | 40 | 0.32 | 0.28 | 0.28 | 0.28 | 0.28 | 0.27 | — |
| Potassium phosphate monobasic pH 6.5 | 5 | 0.30 | 0.00 | — | — | — | — | — |
| | 25 | 0.28 | 0.00 | — | — | — | — | — |
| | 40 | 0.27 | −0.02 | — | — | — | — | — |

TABLE 11

Absorbance readings at 680 nm for soyflour extracts over weekend

| Buffer, initial pH | Temperature (° C.) | Absorbance (680 nm) at time point t (mins) | | | | | | |
|---|---|---|---|---|---|---|---|---|
| | | t = 0 | t = 1 | t = 2 | t = 3 | t = 4 | t = 5 | t = 6 |
| Sodium acetate, pH 4.5 | 5 | 0.36 | 0.00 | — | — | — | — | — |
| | 25 | 0.37 | −0.02 | — | — | — | — | — |
| | 40 | 0.37 | −0.01 | — | — | — | — | — |
| Sodium borate, pH 9.0 | 5 | 0.36 | 0.21 | 0.10 | 0.04 | 0.01 | 0.00 | — |
| | 25 | 0.37 | 0.34 | 0.33 | 0.34 | 0.34 | — | — |
| | 40 | 0.37 | 0.33 | 0.34 | 0.34 | 0.34 | 0.36 | — |
| Potassium phosphate monobasic pH 6.5 | 5 | 0.39 | 0.00 | — | — | — | — | — |
| | 25 | 0.37 | −0.01 | — | — | — | — | — |
| | 40 | 0.41 | 0.02 | — | — | — | — | — |

The only noticeable difference was a reduction in the activity of the pH 9.0 borate extract at 5° C. It was also observed that a filtered extract (pH 4.5) left standing at room temperature over the weekend did not show a significant drop in activity as judged by the methylene blue bleaching method.

Further extractions were conducted at pH 4.5 and 6.5 (loading of 1: 5 w/v soyflour) and at a temperature of 30° C. (Table 12). The extract solutions were assayed using the more sensitive conditions (30 μL of enzyme solution) (cf. Table 4).

It was observed that the supernatant of the pH 4.5 extraction solution was less cloudy than those obtained at both pH 6.5 and 9.0.

TABLE 12

Absorbance readings at 680 nm for 1 and 2 hour soy flour extractions (1:5 w/v) (30° C.)

| Buffer, initial pH | Temperature (° C.) | Absorbance (680 nm) at time point t (mins) | | | | | | | | | | |
|---|---|---|---|---|---|---|---|---|---|---|---|---|
| | | t = 0 | t = 0.5 | t = 1.0 | t = 1.5 | t = 2.0 | t = 2.5 | t = 3.0 | t = 3.5 | t = 4.0 | t = 4.5 | t = 5.0 | t = 5.5 |
| Sodium acetate, pH 4.5 | 30 (1 hr) | 0.35 | 0.35 | 0.29 | 0.13 | 0.08 | 0.00 | — | — | — | — | — | — |
| | | 0.37 | 0.35 | 0.30 | 0.13 | 0.02 | 0.03 | 0.01 | 0.00 | — | — | — | — |
| | 30 (2 hr) | 0.31 | 0.31 | 0.25 | 0.09 | 0.03 | 0.01 | — | — | — | — | — | — |
| | | 0.31 | 0.30 | 0.23 | 0.11 | 0.03 | 0.02 | 0.00 | — | — | — | — | — |
| Potassium phosphate monobasic pH 6.5 | 30 (1 hr) | 0.35 | 0.33 | 0.20 | 0.04 | 0.00 | — | — | — | — | — | — | — |
| | | 0.30 | 0.30 | 0.17 | 0.06 | 0.01 | — | — | — | — | — | — | — |
| | 30 (2 hr) | 0.32 | 0.30 | 0.22 | 0.10 | 0.01 | — | — | — | — | — | — | — |
| | | 0.31 | 0.30 | 0.22 | 0.11 | 0.01 | — | — | — | — | — | — | — |

By comparison of these results with the results of the dilution series of purified enzyme (Table 2), it was determined that ≥0.105 Munits of enzyme activity/mL was extracted from the soy flour over the pH range studied. This is approximately ¼ of the enzyme activity (0.41 Munits/mL of reaction mixture) utilised in the synthesis of the 500 g tox batch. It would appear that at pH 9.0, extraction at 25 and 40° C. reduces the enzyme activity, becoming noticeable after 2 hours extraction time. At the lower pH values of 4.5 and 6.5, extraction at the elevated temperatures does not have a determinable effect under these conditions.

The 14-hour extraction samples were agitated over a weekend under the appropriate conditions and analysed, as before (Table 11).

The extract solutions (1:10 w/v) which had been left over weekend at 25° C. were filtered after standing for 1 day. The sample at pH 4.5 had a clear yellow supernatant, which was decanted and filtered through a pad of Celite. The residual flour was also filtered to give a solid cake. 20 mL extract was recovered from an initial buffer volume of 33 mL. The samples at pH 6.5 and 9.0, which had cloudy supernatants, were treated as above. When decanting the pH 6.5 extract, the supernatant became mixed with the flour residues. The suspension was filtered to give 14 mL of slightly turbid yellow filtrate. The pH 9.0 extract gave 20 mL of an orange coloured turbid filtrate. The pH 4.5 extract at 30° C. (1:5 w/v) was also filtered to give only 4 mL of filtrate from an initial buffer volume of 13.5 mL.

Extraction at pH 4.5 and 6.5 gave enzyme activities of between 0.21 to 0.42 Munits/mL, based on time taken to bleach the methylene blue solution. However, at pH 4.5 a clearer extract can be obtained. At pH 9.0, extract activities appear to decrease over time, and again the extracts obtained are cloudy. At a flour loading of 1:5 w/v, only a small amount of extract can be recovered and the increase in activity over the 1:10 w/v extracts is not significant. Thus a 1:10 w/v loading of soy flour in pH 4.5, 0.1M sodium acetate buffer can be extracted at room temperature to give useful activities.

Example 10

Figure 4:
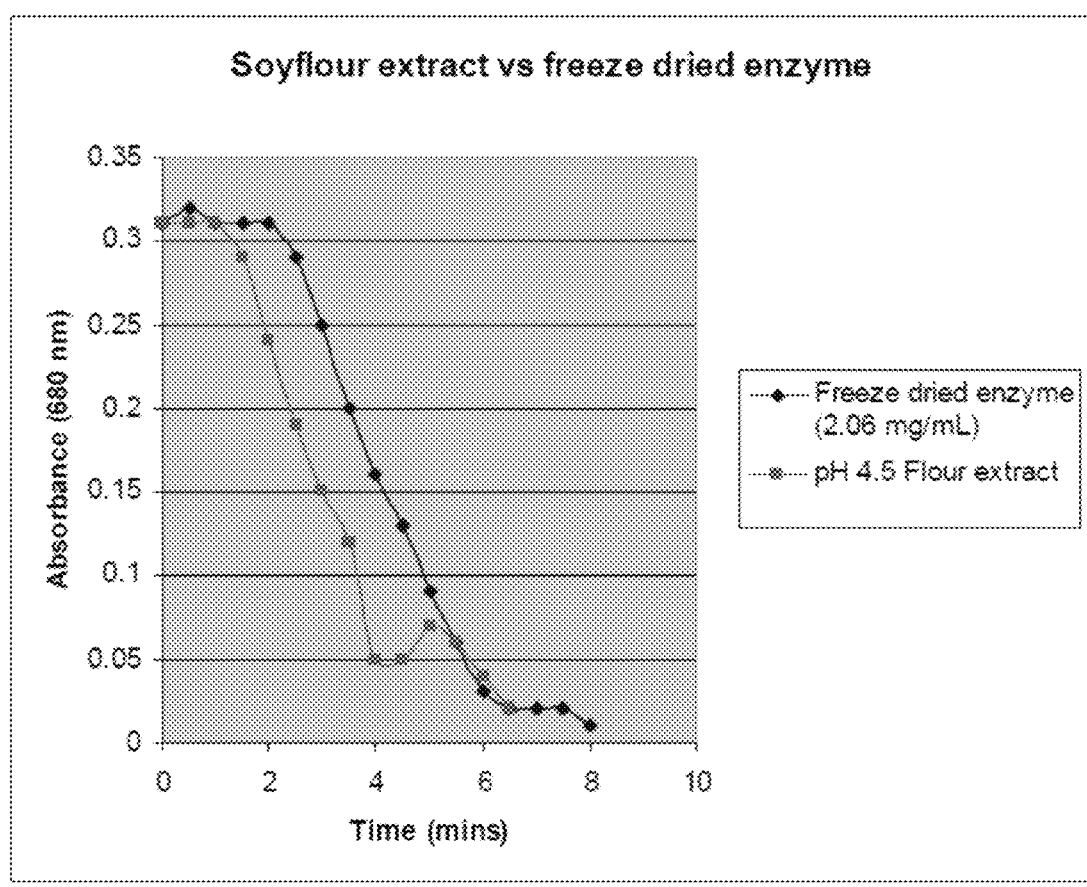
FIG. 4 illustrates the time taken to bleach methylene blue solution using soyflour extract (0.1 M sodium acetate, pH 4.5) compared to commercial enzyme (2.06 mg/mL, 0.2 Munits/mL) in accordance with one embodiment of the present disclosure.

Soy-Flour Extract as Enzyme Source 10 g of 7B soyflour was extracted with 100 mL 0.1M sodium acetate buffer, pH 4.5 for 3 hours at 32° C., 180 rpm before filtering through Celite to yield 85 mL of a clear, yellow filtrate (pH 5.2). A 30 µL portion was analysed by methylene blue bleaching test and the activity was comparable to approximately 2 mg/mL (0.2 Munits/mL) of purified, freeze-dried enzyme (FIG. 4).

A commercial enzyme loading of ~0.055 Munits/mL of reaction solution (1.8 Munits/g DGLA) was sufficient for reaction completion.

Figure 5:
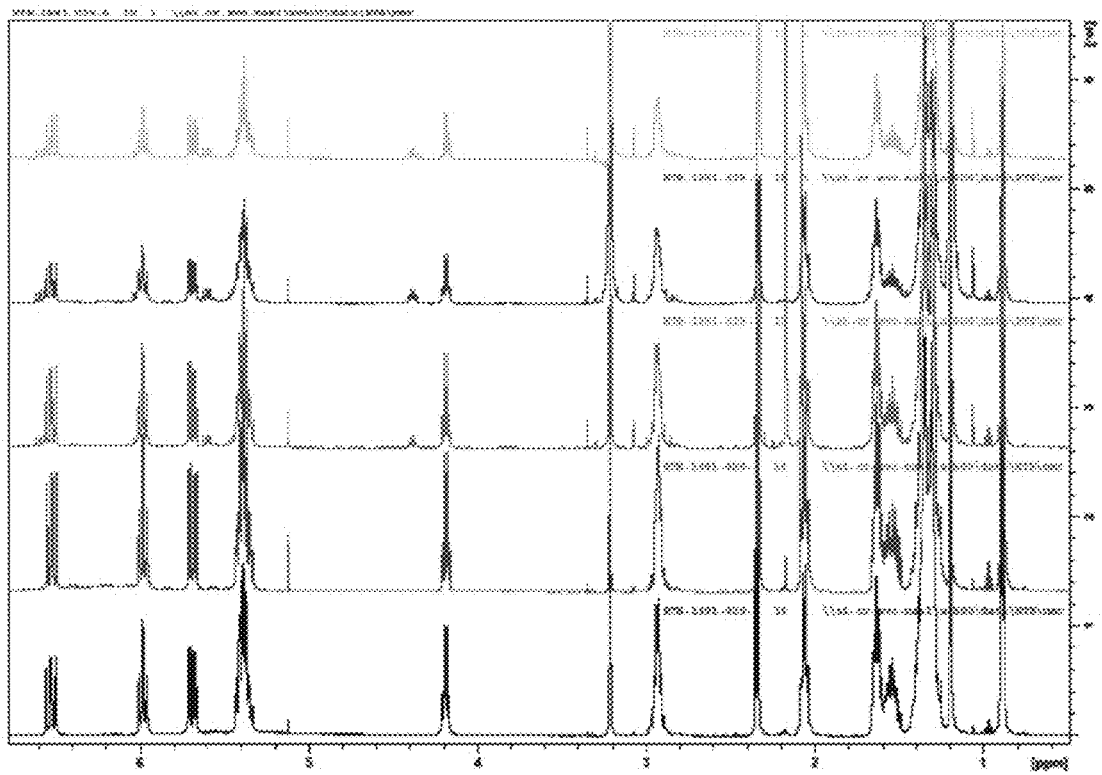
FIG. 5 is an overlay of $^1$H NMR spectra for 1891-029 (yellow: after 1 hour under $O_2$, purple: after 2 hours under $O_2$, green: after 3 hours under $O_2$, + further 0.5 eq cysteine), red: stirred under atmospheric conditions over weekend, with further 0.5 eq of cysteine, blue: isolated crude HETrE)

2 equivalents of cysteine were charged to a Parr reactor along with 35 mL of 0.1 M sodium borate buffer and cooled to 0-5° C. in an ice bath. The pH was adjusted with 2M sodium hydroxide solution, followed by addition of DGLA and further pH adjustment to 9.6. Soy-flour extract (53 mL) was added giving a volume of 100 mL and a pH of 9.3. Enzyme activity loading was 0.11 Munits/mL of reaction solution. The reaction was conducted for 1 hour under $O_2$ pressure (35 psi, 2.5 bar). $^1$H NMR spectroscopy showed little residual DGLA and a mixture of HPETrE and HETrE (FIG. 5). Addition of a further 1 equivalent of cysteine, in 2 portions, allowed reduction of remaining HPETrE as judged by $^1$H NMR spectroscopy. The reaction solution was stored over the weekend at 4° C. The reaction was worked-up as before (FIG. 5).

Example 11

Isolation and Purification of 15(S)-HETrE

Use of cysteine reducing agent allowed reduction of the enzyme activity loading for the reaction by a factor of 7.6 (13.7 Munits to 1.8 Munits/g DGLA), yet giving an acceptable impurity profile. Reaction completion could be obtained within a few hours. Instead of acidifying with 10% citric acid solution, the reaction was acidified with solid citric acid, thus reducing the total volume by ~30%. HETrE product precipitated from the reaction mixture, along with cystine residues, which could be collected by filtration. Slurrying the collected precipitate with MtBE and filtration, followed by removal of the solvent, allowed isolation of >100% weight crude HETrE. In contrast, the previous work-up had involved extraction with a comparatively expensive 50/50 hexane/MtBE mixture (×3) to reduce emulsion formation. A rag layer was also collected which required filtration through celite to break up the emulsion and washing through with MtBE to recover product. Crude HETrE (430 g) was recovered from ~72 L of solvent. However, by this method, 320 g of crude HETrE was recovered from only 9 L MtBE.

Purification by column chromatography (~55 g output) using a 1:10 w/w crude HETrE:silica gel ratio and eluting with (1) 4 L of 10% MTBE:Cyclohexane, (2) 3 L of 20% MTBE:Cyclohexane, and (3) 4 L of 50% MTBE:Cyclohexane (total eluent volume: 11 L) proved suitable. Previously, a Biotage KP Sil column was used to purify ~45 g of 15(S)-HETrE using a 1:10 w/w crude HETrE:silica gel ratio and was eluted with (1) 2 L of Hexane, (2) 2 L of 10% MTBE:Hexane, (3) 2 L of 20% MTBE:Hexane, (4) 2 L of 30% MTBE:Hexane, (5) 4 L of 40% MTBE:Hexane, (6) 50% MTBE:Hexane, and (7) 4 L of MTBE (total eluent volume: 19 L). The improved chromatography conditions represent a 40% reduction in solvent volume, decreased processing time (e.g., for solvent removal), and decreased risk of product degradation.

It was observed with the use of cysteine as reducing agent that a solid precipitated from the reaction as it progressed, likely the oxidised form cystine. Initially, the precipitate visible at the end of the reaction was collected by filtration through Celite to give a clear filtrate, before adjusting the pH to 3 using solid citric acid. Further cystine/cysteine precipitates at this stage along with the product. The doughy precipitate could be collected by filtration through a sintered funnel and air dried on the funnel. The 'dough' was then slurried in MTBE (1×100 mL, 3×50 mL) to remove the product, which was collected by filtration and dried over $Na_2SO_4$.

When purified enzyme was used, extraction of the aqueous layer gave an emulsion which settled out rapidly. However, extraction of reactions using flour extract gave a gelatinous emulsion which required filtration through Celite to break up. This could lead to loss of product or increased solvent usage to wash through the filter. It was found that direct filtration of the precipitated product/cystine and slurrying with MTBE avoided this issue. After performing this procedure, the resulting aqueous filtrate (pH 3) from the flour extract reaction (1891-029) was extracted with 100 mL of MTBE, giving a gel like emulsion which was filtered through Celite. TLC analysis of the organic layer showed only a very faint UV active spot and $^1$H NMR of the isolated product (62 mg) showed no HETrE present, thus indicating that filtration of the precipitate is a suitable method for recovery of the HETrE product.

This reaction yielded 2.5 g (94%) of crude HETrE with purity by UPLC area % (252 nm) of 92.73%.

Example 12

10 L Scale Up Reactions

To 10 L scale up reactions were performed (300 g of DGLA each) to yield a combined total of 469 g (74%) of 15(S)-HETrE with a purity by UPLC of 97.2%, after column chromatographic purification, solvent removal and high vacuum drying. The material was found to have a peroxide value of 12.5 mEq/kg, compared to ~90. mEq/kg for a comparative tox batch. An additional 10 L scale-up reaction was performed to yield another 239 g (76%) of 15(S)-HETrE after column chromatographic purification, solvent removal and high vacuum drying.

Example 13

Stability Study

Two 10 L scale-up reactions were performed to process 600 g of DGLA for stability study. These were performed using the conditions shown in Scheme 2.

Scheme 2.

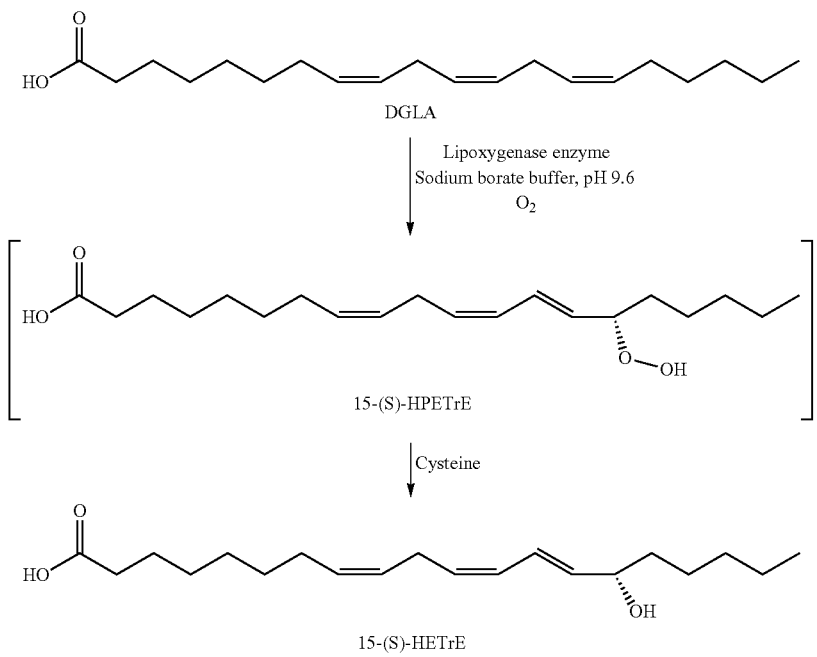

10 L of 0.1 M sodium borate buffer (pH 13.4) was charged to a hydrogenation vessel, followed by 2 equivalents of cysteine. DGLA was charged to the buffer solution and cooled to 0-5° C. LPX1 enzyme powder was added to the cold reaction solution and pressurised with a minimum of 2 bar pure oxygen and stirred for 1 hour. $^1$H NMR analysis after 1 hour showed ~6% HPETrE, and 8% residual DGLA. CAD analysis of the reaction sample showed the residual DGLA to be present at 12.6% w/w. After a further 60 minutes under oxygen pressure, analysis showed ~5% HPETrE by $^1$H NMR and 4% DGLA. CAD analysis showed the residual DGLA to be present at 5.0% w/w. After purging the reaction mixture with nitrogen, a further 1 equivalent of cysteine was added and the reaction was stirred for 1 hour. Analysis of an aliquot showed no HPETrE by $^1$H NMR and 3.5% DGLA. CAD analysis showed the residual DGLA to be present at 3.8% w/w.

The reaction mixture was stirred overnight, under a blanket of nitrogen, at 1.3° C. Analysis of an aliquot showed no HPETrE by $^1$H NMR and 3.5% DGLA. CAD analysis showed the residual DGLA to be present at 5.3% w/w, which is believed to be an anomalous result. An aliquot was worked up under an atmosphere of nitrogen and immediately analysed for peroxide value. This was found to be 2 mEq/kg. The bulk solution was discharged to a 25 L drum and transferred to a 10 L glass vessel, under a nitrogen atmosphere. MtBE containing 0.02% BHT was added and the pH of the aqueous solution adjusted by portionwise addition of solid citric acid. The resulting triphasic mixture (organic, aqueous and solid precipitate) was allowed to settle out. The mixture was then filtered through a 4 L sintered funnel, under a flow of nitrogen. During filtration, which took 1.5-2 hours, approximately two thirds of the added MtBE evaporated. The filtrate layers were returned to the vessel and allowed to settle then separated. The aqueous layer was re-extracted (×2). The three extract layers were concentrated separately on the rotary evaporator. A total of 274 g crude oil was isolated (~231 g (73%) by $^1$H NMR assay against tetrachloronitrobenzene standard). A further 53 g of crude oil (43 g+10 g) was obtained after slurrying the isolated filter cake in MtBE (2×1 L), giving a total crude recovery of 327 g (278 g (88%) by $^1$H NMR assay. Peroxide values of 8.6 mEq/kg and 14.9 mEq/kg were obtained for the first extract and the slurried material, respectively.

A second batch was produced in the same manner, although the initial temperature of the reaction solution was lower 1.4° C. vs 4.2° C. $^1$H NMR analysis after 1 hour showed ~3% HPETrE, and 11% residual DGLA. CAD analysis of the reaction sample showed the residual DGLA to be present at 15.5% w/w. After a further 120 minutes under oxygen pressure, analysis showed ~6% HPETrE by $^1$H NMR and 4% DGLA. After purging the reaction mixture with nitrogen a further 1 equivalent of cysteine was added and the reaction was stirred overnight under a blanket of nitrogen. Analysis of an aliquot showed no HPETrE by $^1$H NMR and ~3% DGLA. CAD analysis showed the residual DGLA to be present at 4.0% w/w.

An aliquot was worked up under an atmosphere of nitrogen and immediately analysed for peroxide value, which was found to be 5 mEq/kg. The bulk solution was discharged to a 25 L drum and transferred to a 15 L glass vessel, under a nitrogen atmosphere. After acidification with solid citric acid to pH 3.2, the resulting solid precipitate was collected by filtration through a porosity 1, 4 L sintered funnel, under a flow of nitrogen. The filter cake was then returned to the vessel and slurried with MtBE (3×3 L) and filtered each time. The three filtrate layers were concentrated separately on the rotary evaporator. A total of 325 g crude oil was isolated (~284 g (90%) by $^1$H NMR assay against tetrachloronitrobenzene standard). A peroxide value of 10 mEq/kg was obtained for the first extract fraction.

The crude materials were combined and purified by column chromatography on numerous 75 L Biotage KP-Sil columns. The purified fractions were combined based on TLC analysis and concentrated on the rotary evaporator at 40° C. (protected from light), before venting with nitrogen and storing at 80° C. The isolated pure HETrE fractions were dissolved in MtBE, filtered through a clean sintered funnel and combined before concentrating on the rotary evaporator at 40° C. (protected from light). The purified material was protected from light and dried on a high vacuum pump for three days at room temperature, before venting with nitrogen and storing at −80° C. A total of 469 g of pale yellow oil was obtained, 97.4% area purity by UPLC (252 nm) and 97.3% area purity using the original HPLC method (235 nm). The $^1$H NMR spectrum conformed to structure. The material was analysed by GC headspace for residual solvent, giving values of 434 and 9.2 ppm for MtBE and cyclohexane, respectively (limits 5000 and 3880 ppm). A peroxide value of 12.5 mEq/kg was calculated for the batch (vs. ~90 mEq/kg for the previous tox batch).

Figure 6:
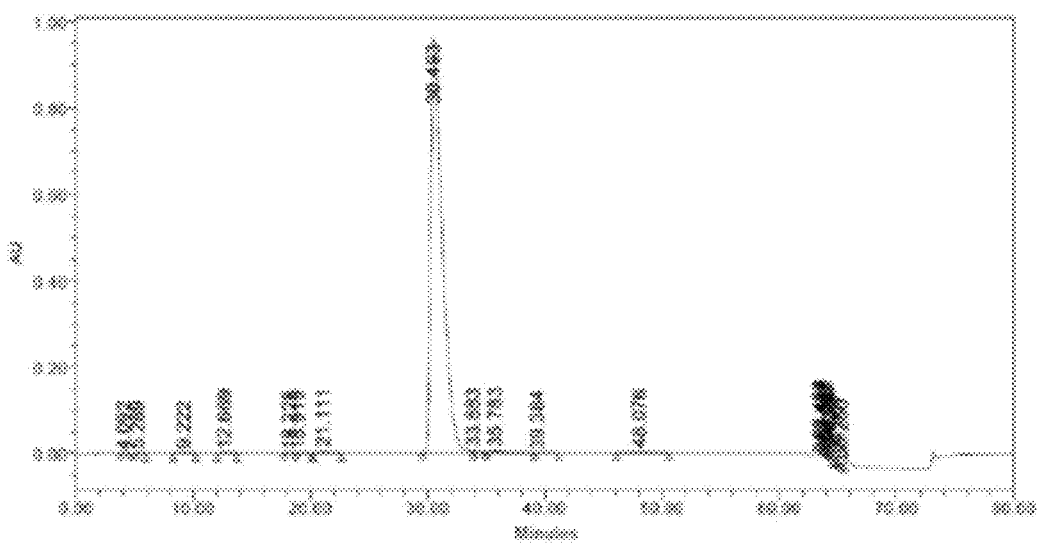
FIG. 6 is an HPLC trace and peak table for 1822-155-4D1.
Figure 7:
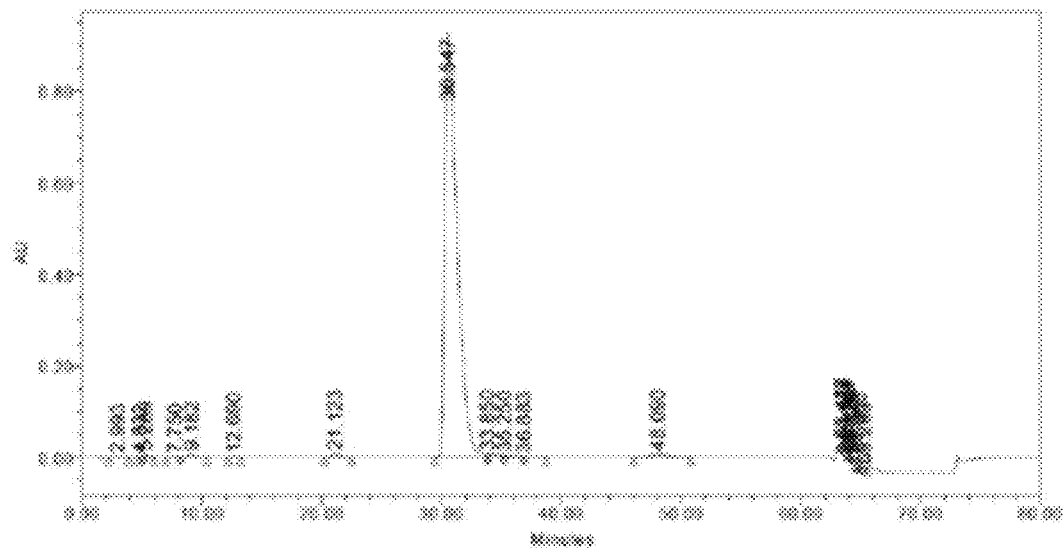
FIG. 7 is an HPLC trace and peak table for 1891-051-7A.

A comparison of the material produced by this method was made with a tox batch by HPLC using the original OPRD method. The HPLC traces are shown in FIG. 6 and FIG. 7.

Figure 8:
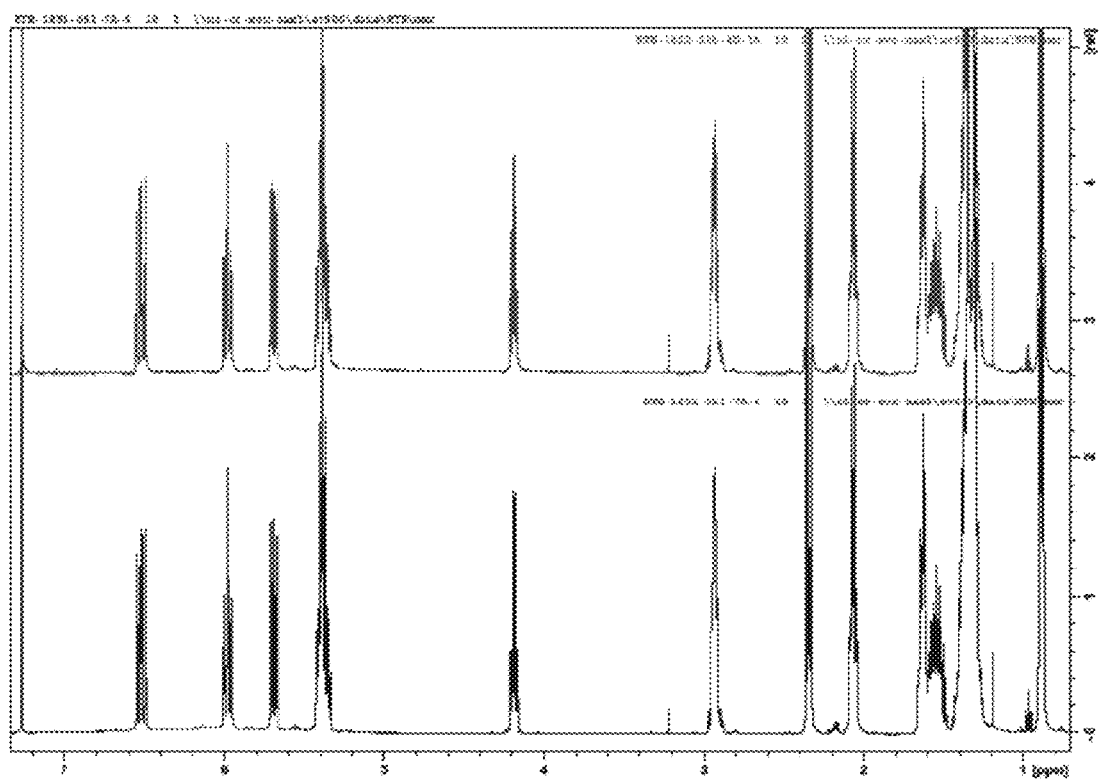
FIG. 8 is an overlay of $^1$H NMR spectra of batch 1822-155-4D1 (red, original method) and batch 1891-051-7A (blue, method according to the present disclosure).

The batches have similar profiles and purities. A major discrepancy between the two spectra is noted at ~35-36 mins, but this is probably due to integration of the broad, ill defined peaks. The impurity at 48.1 mins is present at 0.92% in the test batch vs 0.55% in the tox batch, which may be due to the modified reaction conditions, or more likely due to the composition of the DGLA starting material (a tocopherol stabilized batch was used to prepare the test batch). The impurities between 63 and 66 minutes correspond, with variations in area %. No new impurities above 0.1% are apparent from a comparison of the traces. An overlay of the $^1$H NMR spectra showed a virtually identical profile (FIG. 8).

Table 13 gives a brief comparison of the previously utilized conditions for preparation of the tox batch with the conditions used to prepare the test batch.

TABLE 13

Comparison synthetic methods

| Parameter | Tox Batch | Test Batch |
| --- | --- | --- |
| DGLA input | 1100 g | 600 g |
| Enzyme loading | 13.7 Munits/g | 1.8 Munits/g |
| Purified HETrE output | 603.5 (53%) | 469 (74%) |
| Purity, UV area % | 96-97.5% (235 nm) | >97% (252 nm) |
| Purification solvent usage | 19 L/column | 11 L/column |

It was observed during the performance of scale-up test batches that ~4-5% residual DGLA was left in the reaction mixture after 2.5-3 hours under $O_2$ pressure. During the trial reactions, the last equivalent of cysteine reducing agent was added and stirred under atmospheric conditions, allowing further conversion of residual DGLA to occur. However, in the scale-up reactions the final equivalent of cysteine was added after the reaction mixture had been purged with nitrogen, so no further reduction of DGLA levels was possible. The rationale was to reduce oxygen present in the reaction mixture and thus minimize the likelihood of further peroxide formation and oxidation of cysteine. Further trials were conducted where a further 20-50% of enzyme activity was added. Addition of 20% enzyme activity along with the final equivalent of cysteine was found to give <1% residual DGLA as judged by $^1$H NMR.

The remaining 10 L run was performed according to the process description detailed herein. A total of 239 g of pale yellow oil was obtained with $^1$H NMR profile as before.

Example 14

Process Description

A process description (PD) was generated based on the results of reactions performed during this body of work. A draft process description was followed in the processing of 2×300 g of DGLA to provide sufficient HETrE for the stability study project. The PD comprises the following exemplary steps:

1. Prepare sodium borate buffer 0.1 M by charging of boric acid (61.8 g, 1 mol) and NaOH (120.0 g; 3 mol) to 10 L of water and stirring until dissolved.
2. Charge 10.0 L of 0.1M sodium borate buffer to a hydrogenation vessel.
3. Charge cysteine (237.2 g; 1.958 mol; 2.0 eq) and stir until dissolved
4. Charge DGLA (300.0 g; 9.79 mol; 1.0 eq/wt/vol) to the buffer solution and cool to 0-5° C.
5. Using a calibrated pH probe check that pH is ~9.3-9.6.
6. Adjust pH with 4M NaOH solution, if required.
7. Charge LPX1 enzyme powder (5.30 g, 17.7 mg/g DGLA; 1.8 Munits/g DGLA, 1.77 wt %) to the cold reaction solution.
8. Pressurise reaction vessel with a minimum of 2 bar pure oxygen.
9. Stir the reaction under 2 bar oxygen pressure, at 0-5° C. for 1 hour.
10. Slowly release the oxygen pressure to avoid foaming.
11. Chemist check: Remove an aliquot; acidify the extract to pH 3, using solid citric acid and extract with MTBE. Dry over $Na_2SO_4$, filter and remove the solvent on the rotary evaporator and analyse the residue by $^1$H NMR to confirm conversion of DGLA to HPETrE/HETrE.
12. Add further LPX1 enzyme powder (1.06 g, 3.5 mg/g DGLA, 0.36 Munits/g DGLA, 0.35 wt %) and 1 equivalent of cysteine (119.0 g; 0.979 mol) and stir under oxygen for a further 1.5 hrs.
13. Analyze for Oxidation completion—Remove an aliquot of the reaction mixture, quench with an equal volume of MeOH, and analyse by CAD detection to show consumption of starting material. PASS if residual DGLA <10 g/kg (by HPLC/CAD). If IPC fails, then continue agitation under oxygen pressure for another hour and repeat analysis.
14. Analyze for Reduction completion—Remove an aliquot; acidify the extract to pH 3, using solid citric acid and extract with MTBE. Dry over Na2SO4, filter and remove the solvent on the rotary evaporator and analyse the residue by $^1$H NMR and/or UPLC/UV to confirm no residual HPETrE. During trial phase, protect sample from oxygen and conduct peroxide test without delay. Pass if no 15-HPETrE detectable by NMR and/or UPLC/UV. Peroxide value is FIO. If IPC fails then add cysteine (59.5 g, 0.489 mol, 0.5 eq) and continue agitation under nitrogen blanket for another 4 to 8 hours and repeat analysis.
15. Purge the reaction mixture with nitrogen (×3).
16. Transfer reactor contents to a 25 L drum under a flow of nitrogen.
17. Charge reaction mixture to nitrogen-blanketed ~15 L vessel.
18. Charge solid citric acid (as required, charge table (Table 16, Appendix 1) as guide only) in portions to the agitated, nitrogen-blanketed reaction mixture, checking pH with a calibrated pH meter. Adjust to pH 3.5. Wait for pH to stabilise prior to adding each next portion. Record addition times, pH trend and observations.
19. Stop agitation and filter the precipitated solid on a sintered funnel. Apply external nitrogen blanketing during filtration.
20. Transfer aqueous filtrate layer into 10 L drum.
21. Transfer wet cake back into extraction vessel. Charge MtBE (3 L) to extraction vessel.
22. Agitate for 10 min and allow to settle.
23. Stop agitation and filter the precipitated solid on a sintered funnel. Apply external nitrogen blanketing during filtration.
24. Transfer organic filtrate to a clean 10 L drum.
25. Repeat steps 21 to 24, twice more.
26. Evaporate crude product solution until distillate collection becomes slow at 250 mBar/40 deg C. bath. Vent rotavap with nitrogen. Before evaporation end, transfer solution into tared 1 L flask. Protect from air as good as possible.
27. Determine crude weight, and take NMR sample for 15-HETrE:MtBE molar ratio (FIO). Take FIO sample for peroxide test when fresh and analyse without delay. Take FIO sample for crude purity by UPLC/UV.
28. Store crude product under nitrogen at −80 deg C.
29. Dissolve crude HETrE in 80 g portions in 1 volume of cyclohexane and apply to a Biotage 75 L silica cartridge, pre-eluted with cyclohexane. Elute the product from the column starting with 10% MtBE: cyclohexane up to 50% MtBE: cyclohexane.
30. Pre-combine product fractions based on TLC
31. Analyze Column fraction purity -Remove an aliquot of pre-combined product fractions and analyse by UPLC. PASS if % area purity >95%. If IPC fails, set-fractions aside for repurification.
32. Combine suitably pure product containing fractions.
33. Remove the solvent on the rotary evaporator at 40° C. Vent with nitrogen.
34. Dry the material to constant weight under high vacuum, with stirring.
35. Release vacuum under nitrogen.
36. Analyze Residual solvents -Remove an aliquot of dried product and analyse by GC-headspace. PASS if residual solvents are below ICH limits (<5000 ppm MtBE, 3880 ppm cyclohexane). If IPC fails, return bulk material to high vacuum pump and continue drying for 24 hours and repeat analysis.
37. Transfer to a tared, amber bottle under a blanket of nitrogen and store at 80° C.

Example 15

Reactor Cleaning

DGLA and HETrE residues are readily soluble in alcohols such as ethanol and methanol, or acetone. Cysteine is soluble in water (280 g/L @ 25° C.) and ethanol (1.5 g/100 g of ethanol @ 19° C.) and cystine is soluble in 1M HCl with heating (50 g/L) and basic solutions.

550 mg of the solid collected from a reaction work-up was slurried in 12 mL of 1M HCl with heating. The bulk of the material dissolved with heating at 50° C. A small amount of insoluble material was visible. Addition of further 1M HCl (12 mL) did not allow dissolution of the sticky solid. The residual material was collected by filtration (14 mg, wet, 2.5%).

550 mg of the collected solid was slurried in 10 mL of 4M NaOH with heating (heat gun). The bulk of the material dissolved but again a small amount of insoluble material was visible.

Addition of further NaOH (10 mL) did not allow dissolution of the solid.

After performance of the 10 L reactions, the hydrogenation vessel was cleaned with water and methanol to remove precipitated cysteine/cystine, etc. After work-up of the reaction mixture in a 15 L glass vessel, the reactor was cleaned with a caustic solution (~0.5M), heated to 80° C. and stirred overnight, followed by a rinse with acetone to leave the vessel visually clean.

Example 16

Thermal Hazard Assessment

The Advanced Reactive System Screening Tool (ARSST) is an effective calorimeter that can quickly and safely identify potential chemical hazards in the process industry.

The synthesis reaction (Scheme 2) involves the peroxidation of DGLA using lipoxgenase enzyme in sodium borate buffer. The resulting peroxide (15-(S)-HPETrE) is then reduced, in situ, to the final product 15-(S)-HETrE in the presence of cysteine. The reaction is intended to be carried out as a 1 pot procedure at 0-5° C. The main concern was that elevated temperatures could bring about adverse thermal events particularly as peroxide is formed during the course of the reaction.

All the reagents were charged to the ARSST cell as an aqueous solution that had been prepared in the lab. The solution strength was approximately 5% w/w of the starting reagents.

Approximately 10 g of the solution was transferred to the ARSST vessel in one lot, the pressure pad was applied and the run started. The run was to be stopped at 250° C. to avoid boiling off water.

Figure 9:
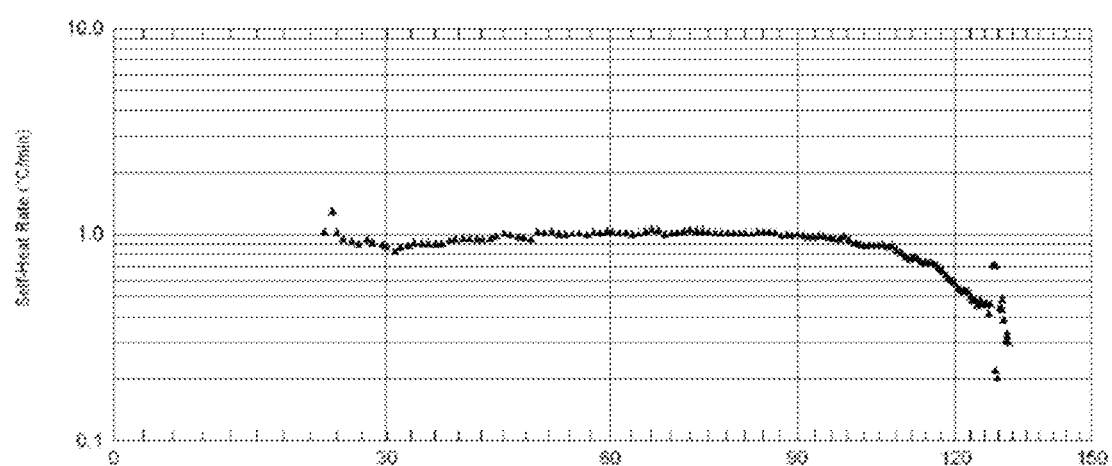
FIG. 9 shows heat rate data for HETrE reaction according to one embodiment of the present disclosure.

The temp in the vessel was 21° C. before addition. The self heat rate was approximately 0.9° C./min. There were no significant exotherms observed during the course of the reaction (FIG. 9). No thermal hazards were observed using Advanced Reactive System Screening Tool (ARSST) or Direct Scanning calorimetry (DSC).

Figure 10:
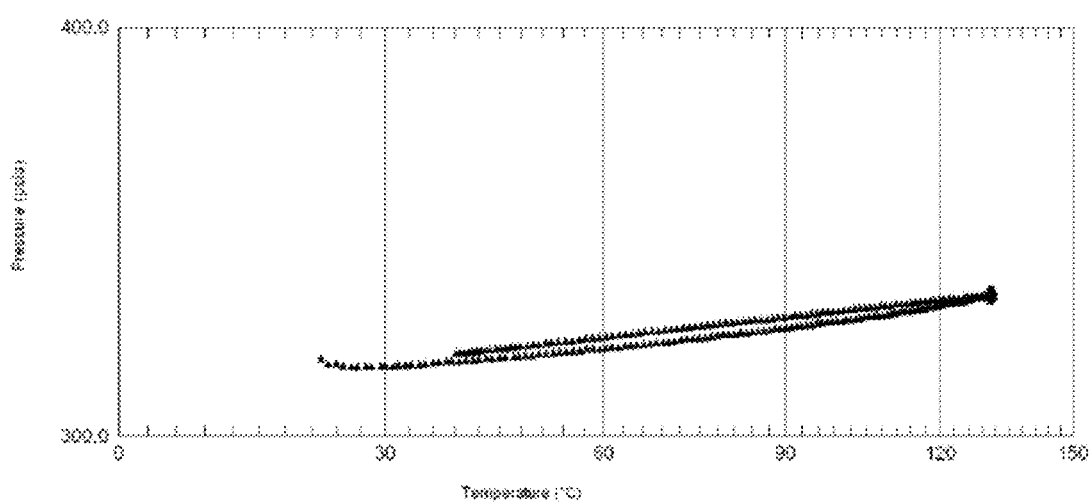
FIG. 10 is a plot of pressure vs. temperature for an HETrE reaction according to one embodiment of the present disclosure.

No further exothermicity was observed within the test range (up to 140° C.). No gas evolution was observed during the course of the run. The self heat rate declined at 100° C. due to the formation of volatile compounds possibly from the decomposition of the products, permanent gas formation was not observed (FIG. 10).

Figure 11:
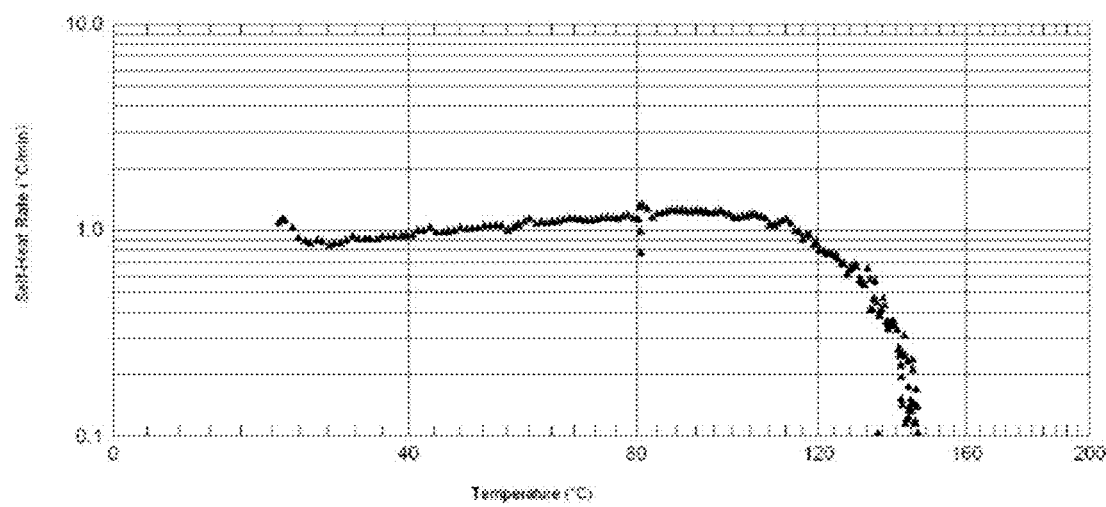
FIG. 11 shows heat rate data for an HPETrE reaction according to one embodiment of the present disclosure.

A further run was carried out using a reaction solution (~10 g) where the cysteine reductant had been omitted and thus contained predominately the intermediate peroxide, as any potential thermal hazards were most likely to be observed in this case (FIG. 11).

Figure 12:
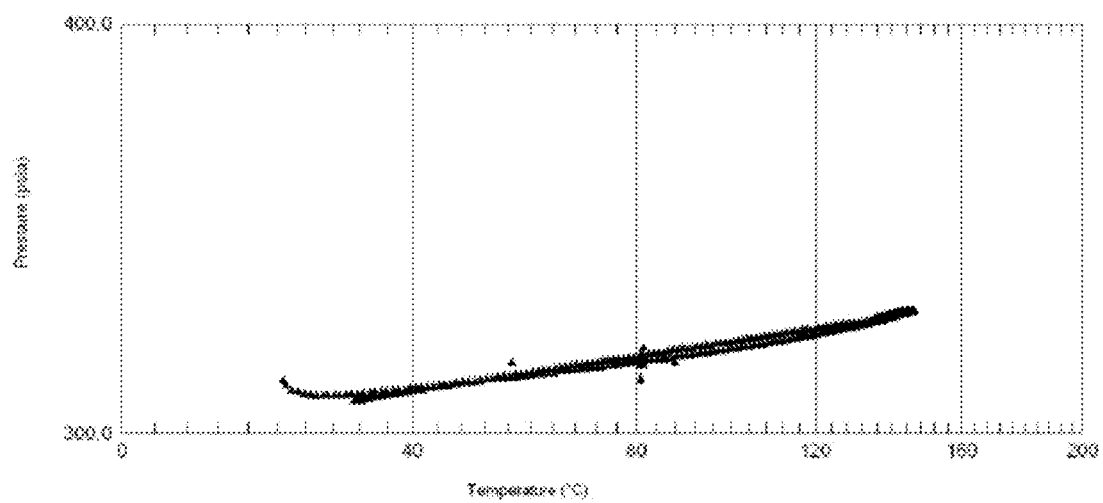
FIG. 12 is a plot of pressure vs. temperature for an HPETrE reaction according to one embodiment of the present disclosure.

An exotherm was detected that had an onset temperature of 40° C., the ATR was 13° C. Background heating rate was 0.9° C./min. At approximately 116° C. the self heat rate began to decline due to the formation of volatiles, likely to be decomposition of the product. As before, there was no evidence for any emission of gas in this reaction (FIG. 12).

An exotherm with an onset temperature of 40° C. and a n ATR of 13° C. was observed in this reaction. It is not likely to be a concern as the reaction is to be run at 0-5° C. As peroxide levels are low during the reaction it is unlikely that the observed exotherm will be apparent under standard reaction conditions. No visible gas emission was observed in this reaction. The reaction is safe to operate at the proposed temperature range of 0-5° C.

Samples of neat HETrE were analysed by DSC with heat rates of 2, 5, 10 and 20° C./min over a range from 20 to 300° C. No significant exotherms were observed although a slight endotherm was observed at ~40° C., which was probably due to residual solvent (MtBE) evaporating from the sample.

Example 17

Robustness Studies

Using the modified process, extended reaction times under $O_2$ (up to 4 hours) did not show any adverse impact on product quality.

Extended time (4.5 days) refluxing in 40% MtBE: cyclohexane at an external temperature of 75° C. did not cause significant degradation of HETrE. Previously, neat HETrE heated at 50° C. (1822-129-4E) under vacuum showed degradation (1 major impurity was observed which has since been identified as an ester formed with itself.

Example 18

Investigation of the Stability of 15(S)-HPETrE/HETrE Towards Reaction Time Extension A number of reactions have given useful information with regards to the robustness at various stages of the reaction. These are summarised in Table 14.

TABLE 14

Details of experiments showing reaction robustness

| Experiment | Enzyme loading | Conditions | Results |
|---|---|---|---|
| 1822-163 | (~13.8 Munits/g DGLA) | Original conditions with extended time (4 hours under $O_2$ pressure | Both $_1$H NMR spectroscopy and HPLC analysis showed the presence of dihydroxy triene impurity |
| 1822-193 | (~13.7 Munits/g DGLA) | Stirred under $O_2$ pressure for 1 hour to generate HPETrE before adding 2 eq. cysteine as solution in NaOH (aq) and stirring under $O_2$ pressure for 1 hour, then 2 hours. | Both $_1$H NMR spectroscopy and HPLC analysis showed the presence of dihydroxy triene impurity |
| 1822-195 | (~13.7 Munits/g DGLA) | Added 2 eq. cysteine and stirred under $O_2$ pressure for 0.5 hour. Left reaction standing overnight at 4° C. | Initial $_1$H NMR spectrum showed mixture of HPETrE, HETrE and small amount of residual DGLA. $_1$H NMR spectrum after overnight storage showed increased impurities. |
| 1891-001 | (~3.4 Munits/g DGLA) | Added 2 eq. cysteine and stirred under $O_2$ pressure for 1 hour. Added 1 eq. of cysteine and stirred at atmospheric pressure for 1 hour. Filtered reaction mixture through Celite and adjusted aqueous layer to pH 3. Left reaction standing overnight at 4° C. | Initial $_1$H NMR spectrum showed mixture of HPETrE, HETrE and small amount of residual DGLA. $_1$H NMR spectrum after stirring with additional cysteine showed no HPETrE. $_1$H NMR spectrum after overnight storage showed little DGLA (<1%). HPLC area % purity (252 nm) 93.55%. |
| 1891-009 | (~1.8 Munits/g DGLA) | Fermentor reaction. Bubbled through with oxygen for 6.5 hours. Filtered reaction mixture through Celite and adjusted aqueous layer to pH 3. Left reaction standing at 4° C. over weekend. | $_1$H NMR spectrum after weekend storage showed little DGLA (<1%). HPLC area % purity (235 nm) 96.94%. |
| 1891-051 (2 batches) | (~1.8 Munits/g DGLA) | Added 2 eq. cysteine and stirred under $O_2$ pressure for 2.5-3.75 hours. Added 1 eq. of cysteine and stirred under nitrogen for ~16 hours. Adjusted aqueous layer to pH 3, filtered precipitate. Removed product using MtBE | $_1$H NMR spectrum showed mixture of HPETrE, HETrE and small amount of residual DGLA. $_1$H NMR spectrum after stirring with additional cysteine showed no HPETrE. $_1$H NMR spectrum after overnight storage showed ~3% DGLA. |

Figure 13:
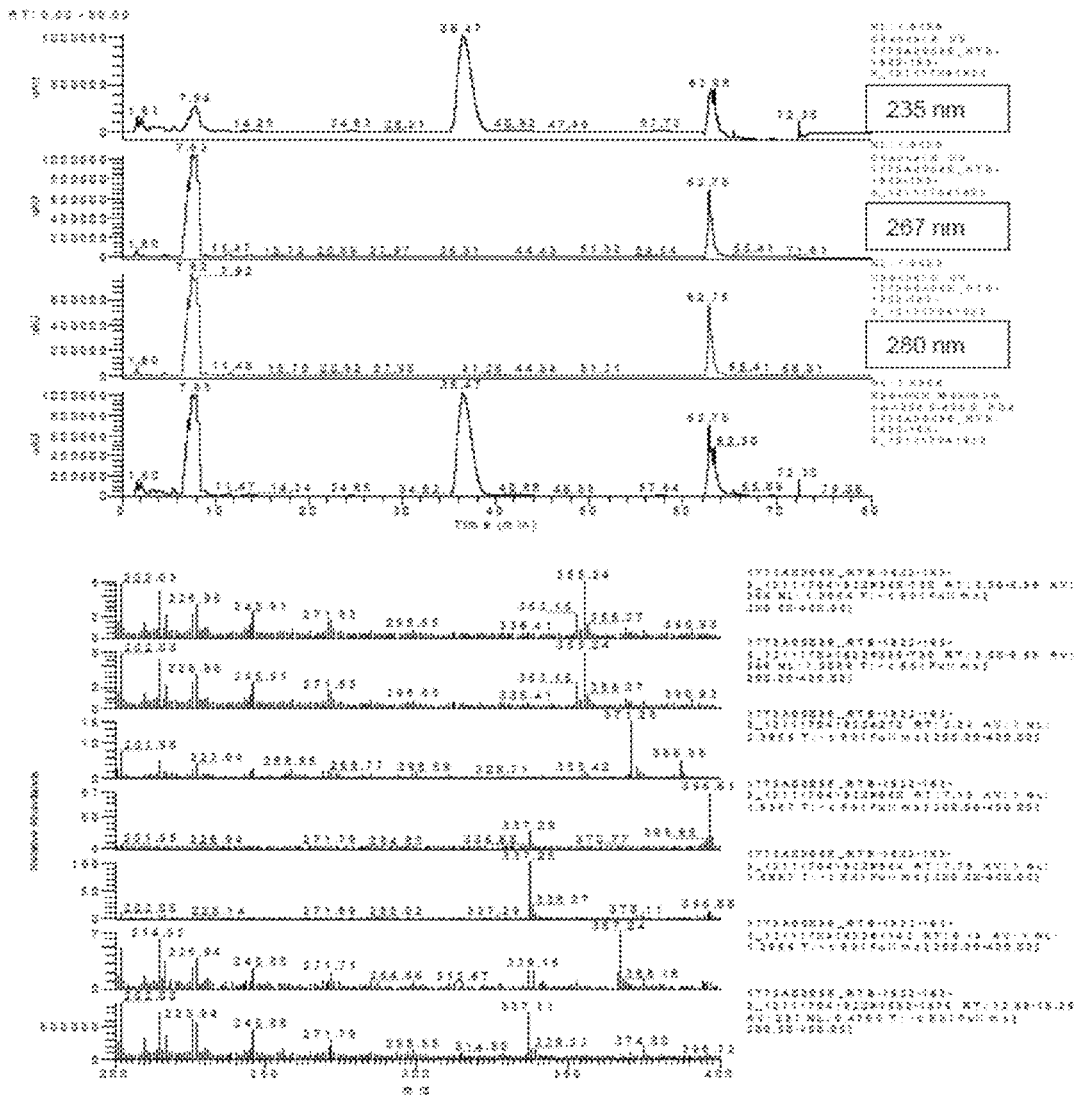
FIG. 13 shows an LC-MS analysis of over-oxidized material 1822-063-3 produced in an embodiment of the present disclosure.

Previously, using the original processing conditions (generation of hydroperoxide followed by reduction to HETrE using sodium borohydride) it was observed that extended times under oxygen pressure (4 hours) lead to the formation of overoxidised impurities (experiment 1822-063) as judged by $^1$H NMR (FIG. 14), and LCMS (FIG. 13). The peak at RT ~7.8 has an m/z of 337, corresponding with di-HETrE and the absorbance is greatest at 267 nm which corresponds with the trienoic nature of the compound.

An initial reaction (1822-193) was performed where the hydroperoxide intermediate was formed using the same enzyme loading as previously (13.7 Munits/g DGLA), before adding 2 equivalents of cysteine reducing agent and stirring under $O_2$/air for a further 3.5 hours. The $^1$H NMR profile (FIG. 14) was similar to that obtained for 1822-163. It appeared that the over-oxidation was occurring with the hydroperoxide intermediate, due either to the high enzyme loading or the reactive nature of the hydroperoxide towards oxygen.

In the next experiment (1822-195), 2 equivalents of cysteine reducing agent was added at the beginning of the reaction, which was stirred under $O_2$ pressure for 30 mins. Some residual DGLA was visible in the $^1$H NMR spectrum, plus a mixture of HETrE and HPETrE and a small amount of the over-oxidised impurity. After storing under atmospheric conditions overnight, the impurity profile appeared slightly worse, with no further reduction of HPETrE, which suggested that the cysteine had all been oxidised either by hydroperoxide or oxygen.

In experiment 1822-197, addition of 3 equivalents of cysteine at the beginning of the reaction appeared to reduce over-oxidation but it also slowed the conversion of DGLA to HETrE. It is postulated that the excess cysteine speeds the reduction of the enzyme activating HPETrE and this could be responsible for the lack of over-oxidation, as well as the sluggish reaction. Experiments 1891-001 to -005 were then carried out where the enzyme loading was reduced to 3.6, 1.8 and 0.9 Munits of enzyme activity/gram DGLA substrate, respectively. 2 equivalents of cysteine were added at the beginning of the reactions which were placed under $O_2$ pressure for 1 hour before analysing by $^1$H NMR and then adding a further 1 equivalent of cysteine and stirring under air or $O_2$ pressure for a further 1 hour. None of the over-oxidised impurity was observed by $^1$H NMR (FIG. 14), although low levels were visible by UPLC at 252 nm.

Fermentor reaction 1891-009, where oxygen was bubbled continuously through the reaction mixture for 6.5 hours, showed no over-oxidised product by $^1$H NMR. In this case, the concentration of active enzyme in the solution was always at a low level.

Figure 14:
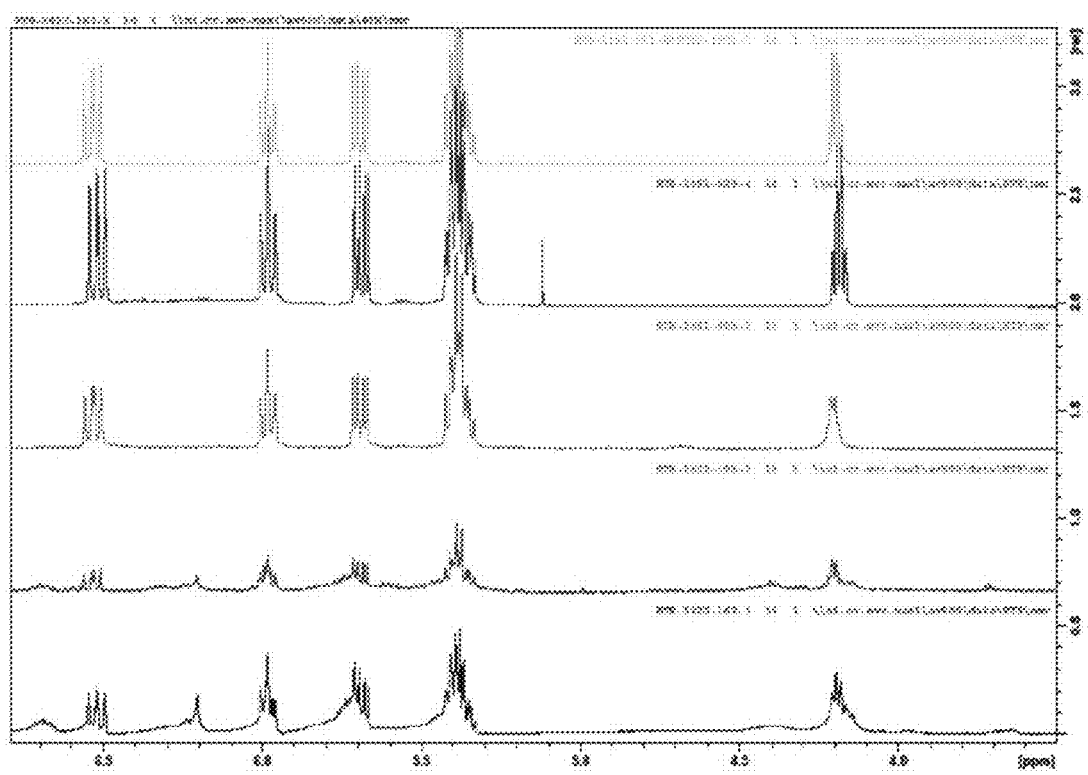
FIG. 14 is an overlay of $^1$H NMR spectra comparing over-oxidized samples (1822-163-3, blue, 1822193-3, red) in reactions according to one embodiment of the present disclosure (1891-003-3, green, 1891-029-4, purple and scale up batch 1891-05, yellow) run for extended periods in the presence of $O_2$/air.

Reaction 1891-029 was stirred under oxygen for 3 hours and stored over weekend under air. An insignificant amount of the over-oxidised impurity was visible by $^1$H NMR (FIG. 14).

Scale-up batches 1891-051 (1.8 Munits/g DGLA) were maintained under $O_2$ pressure for 2.5-3.75 hours with no serious impact on purity as judged by $^1$H NMR analysis.

Example 19

Stability Under Solvent Removal Conditions

A heat stability trial was conducted where a solution of HETrE (~9.1 g) in 500 mL 40% MtBE: cyclohexane was heated at 75° C. (external oil bath temperature) at 400 mbar vacuum (condenser coolant temperature –0° C.). This established a gentle reflux. The solution was protected from light. Samples were withdrawn at various time points, under a nitrogen atmosphere, and analysed by UPLC (252 nm) (FIG. 15).

The conditions were designed to mimic the likely conditions encountered on a plant scale solvent removal from pooled column fractions. After 6 hours, no significant decrease in purity was detected. The reflux was extended over a further 112 hours. No significant decrease in purity was observed, nor was there a rapid increase in the formation of the dimer impurity at RT 12.2 mins, although there was an increase from 0.44 to 0.64%.

Example 20

Investigation of Non-NMR Method for Reaction Completion IPC

Figure 16:
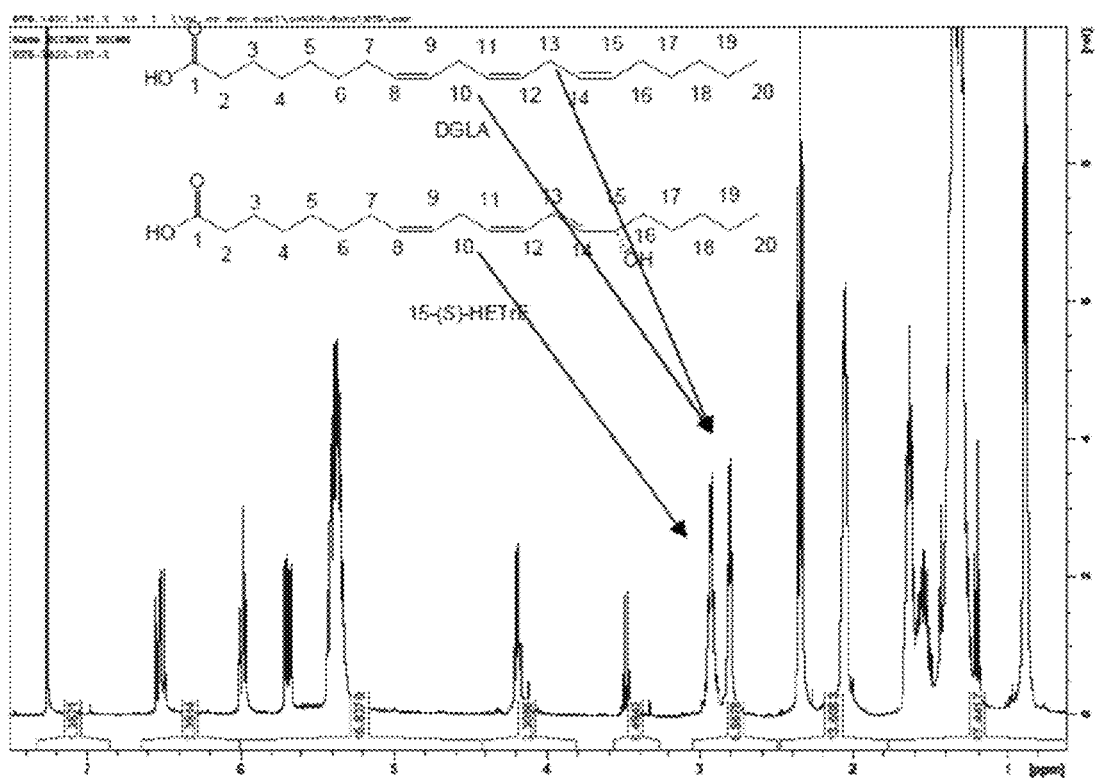
FIG. 16 is a representative spectrum showing overlap between DGLA and HETrE proton signals by $^1$H NMR.
Figure 17:
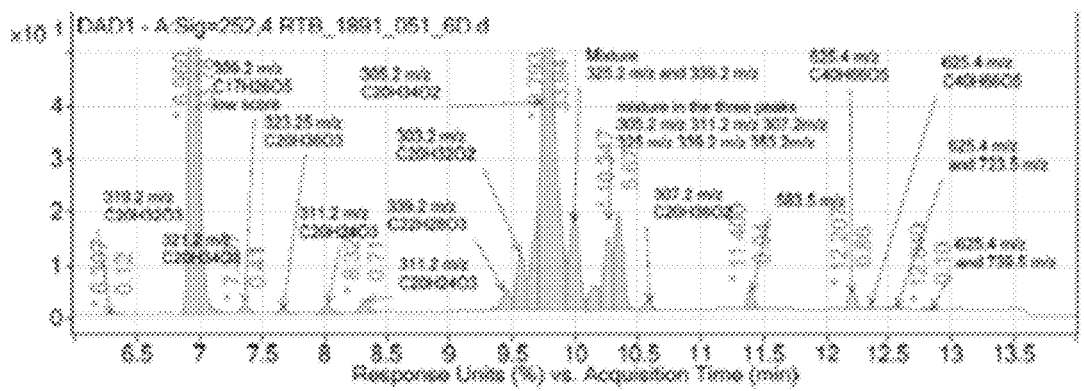
FIG. 17 is an annotated UV chromatogram of front fractions (1891-051-6D) from the purification of 15-(S)-HETrE according to one embodiment of the present disclosure.
Figure 18:
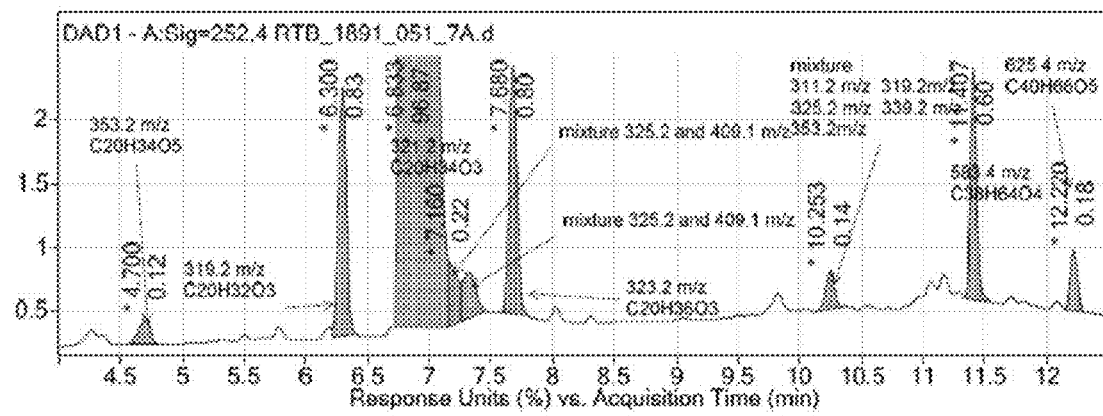
FIG. 18 is an annotated UV chromatogram of purified 15-(S)-HETrE (1891-051-7A) produced according to one embodiment of the present disclosure.
Figure 19:
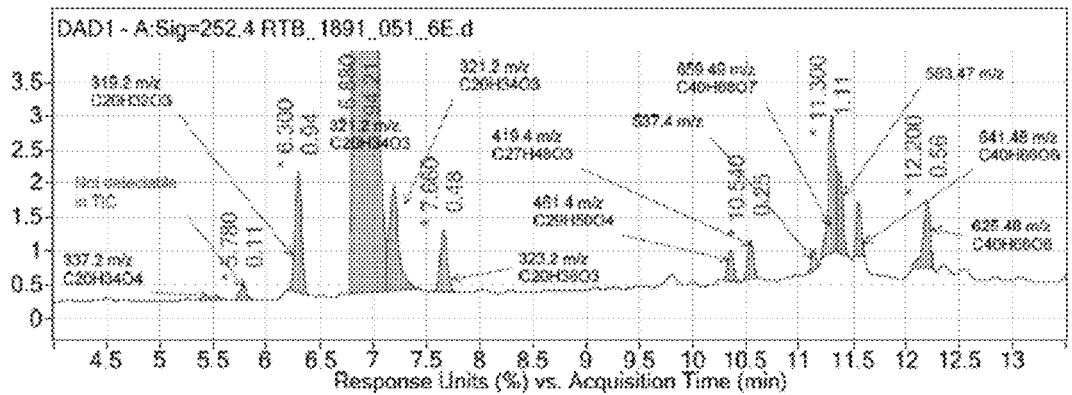
FIG. 19 is an annotated UV chromatogram of tail fractions (1891-051-6E) from the purification of 15(S)-HETrE according to one embodiment of the present disclosure.

A chemical aerosol detection (CAD) method against a w/w DGLA standard was used to determine residual DGLA in reaction mixture. Previous reactions were assessed for reaction completion based on removal of an aliquot from the reaction mixture and mini work-up followed by $^1$H NMR analysis. However, this method was not ideal, as there was some overlap between the residual DGLA and HETrE product signals (FIG. 16).

An alternative method was preferable. As DGLA does not absorb above 210 nm, UV analysis was discounted. Charged aerosol detection (CAD) was found to be a suitable method where the IPC sample would be compared with a 0.1% w/w DGLA standard. The IPC sample would be withdrawn from the reaction and quenched with 50% methanol to denature the enzyme, before the analysis was conducted. This method will allow more accurate determination of residual DGLA levels in reaction samples.

Example 21

LC-MS Investigation of Impurities

Figure 20:
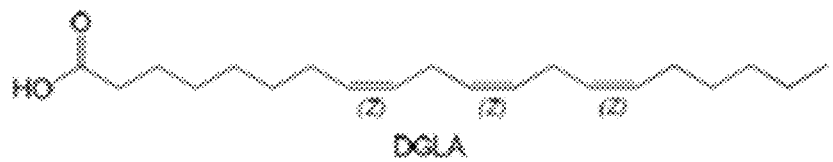
FIG. 20 shows chemical structures and other characteristic data for DGLA and major impurities.
Figure 20:
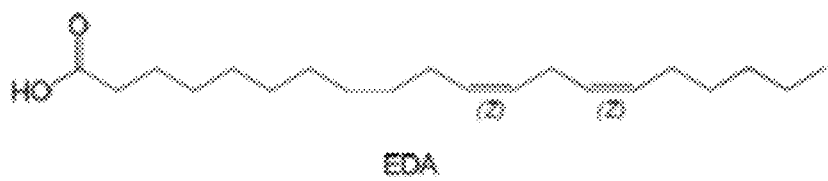
Figure 20:
Figure 20:
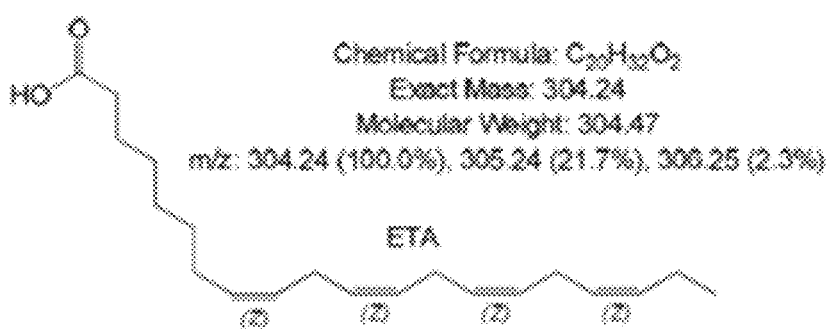

Purified 15(S)-HETrE and impurity enriched front and tail fractions prepared during the course of PRD development were analysed by LC-MS and MS-MS. Based on the supplied specifications for DGLA and the data obtained, tentative structures were suggested for the observed impurities. Based on the specifications of the DGLA starting material, the three major impurities present (FIG. 20) were 20:2ω6 (Eicosadienoic acid (EDA), $C_{20}H_{36}O_2$, RMM 308.48), 20:3ω3 (Eicosatrienoic acid (ETE) $C_{20}H_{34}O_2$, RMM 306.48) and 20:4Ω3 (Eicosatetraenoic acid (ETA), $C_{20}H_{32}O_2$, RMM 304.48) with FAME area % by GC analysis of 1.1, 1.6 and 0.4%, respectively. A further 2 unidentified impurities each at 0.2% area (FAME) area were also present giving total impurities of 3.5 area % by FAME GC analysis.

Figure 21:
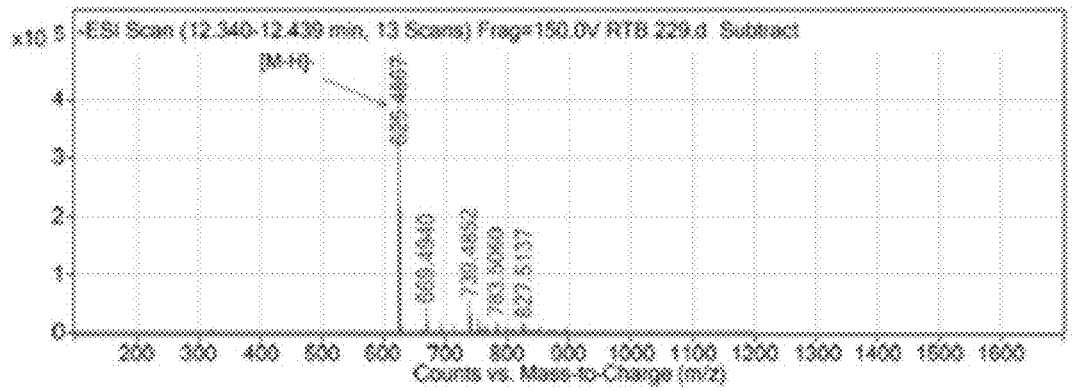
FIG. 21 shows mass spectral data from fragmentation analysis of a dimeric impurity in purified HETrE72.
Figure 21:
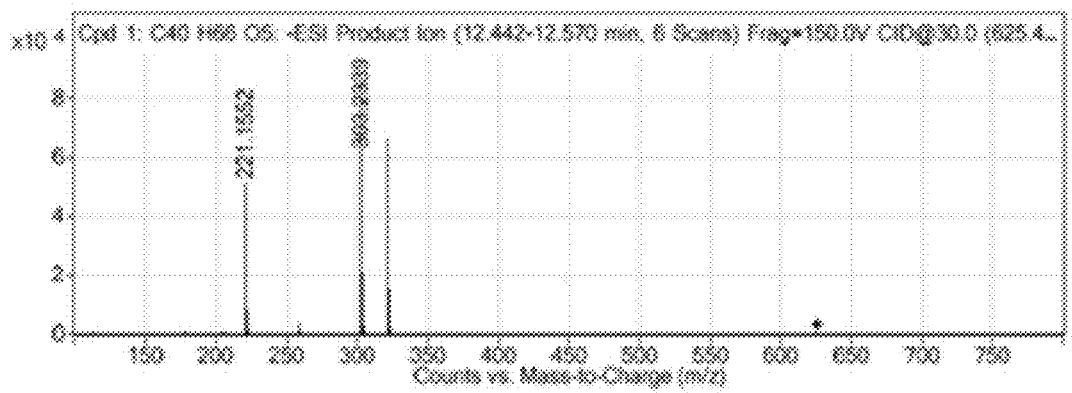

Tentative structures for the identified masses from the purified product (1891-051-7A) are included in Table 15. The major impurities identified in the purified material at m/z 323 (RT 7.68 mins) and 319 (RT 6.3 mins) correspond with the hydroxylated products of EDA and ETA (HEDA and HETE, respectively). No immediately identifiable impurity related to hydroxylation of ETE could be detected (expected m/z 321) in the purified material, although in the tail fractions, a peak with m/z 321(RT 7.19 mins) was observed on the main HETrE product peak. The third major impurity had an m/z of 583 (RT 11.41) which is probably related to the dimeric product visible at 12.22 mins with an m/z of 625. Initially, this was assumed to be formed due to either a Diels Alder mechanism, or self-esterification. LC MS-MS (FIG. 21) was performed on a sample (sample 229 from stability study 1773A0030E) which had been stored at +25° C., in which this dimeric impurity had increased.

TABLE 15

Tentative structures of impurities present in purified 15-(S)-HETrE based on LC-MS and MS-MS analysis

| LC Peak RT (mins) | RRT | % Area purity (252 nm) | Corresponding m/z and suggested mol formula | Potential Structure |
|---|---|---|---|---|
| 4.7 | 0.69 | 0.12 | 353.2 C26H34O5 | 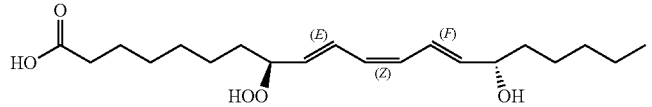 Chemical Formula: $C_{20}H_{34}O_5$<br>Exact Mass: 354.24<br>Molecular Weight: 354.48<br>m/z: 354.24 (100.0%), 355.24 (21.8%),<br>356.25 (2.4%), 356.24 (1.0%) |
| 6.3 | 0.92 | 0.83 | 319.2 C20H32O3 | 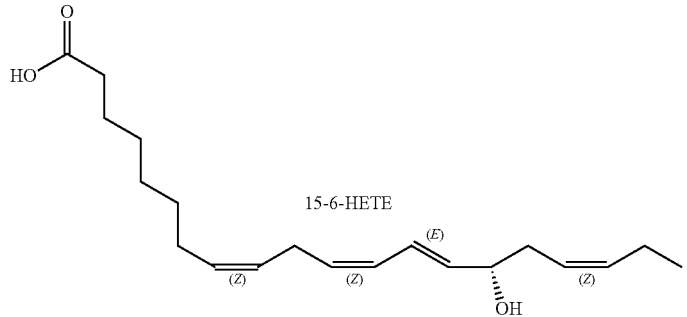 15-6-HETE<br>Chemical Formula: $C_{20}H_{32}O_3$<br>Exact Mass: 320.24<br>Molecular Weight: 320.47<br>m/z: 320.04 (100.0%), 321.24 (22.1%) 322.24 (2.9%) |
| 6.83 | 1.00 | 96.87 | 321.2 C20H34O3 | 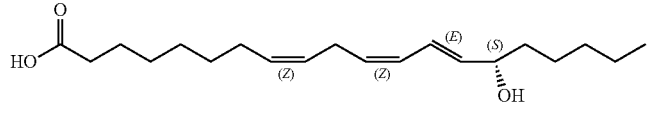 15-(S)-HETrE<br>Chemical Formula: $C_{20}H_{34}O_3$<br>Exact Mass: 322.25<br>Molecular Weight: 322.48<br>m/z: 322.25 (100.0%), 323.25 (21.6%), 324.26 (2.9%) |
| 7.16 | 1.05 | 0.22 | 325.2 and 409.1 | Further investigation required to identify |
| 7.32 | 1.07 | 0.25 | 325.2 and 409.1 | Further investigation required to identify |
| 7.68 | 1.12 | 0.80 | 323.2 C20H36O3 | 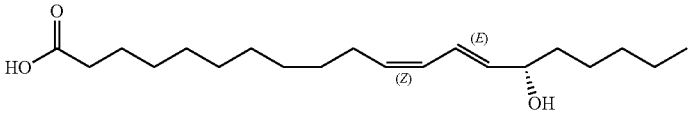 15-(S)-HEDA<br>Chemical Formula: $C_{20}H_{36}O_3$<br>Exact Mass: 324.27<br>Molecular Weight: 324.50<br>m/z: 324.27 (100.0%), 325.27 (22.2%), 326.27 (2.9%) |

TABLE 15-continued

Tentative structures of impurities present in purified 15-(S)-HETrE based on LC-MS and MS-MS analysis

| LC Peak RT (mins) | RRT | % Area purity (252 nm) | Corresponding m/z and suggested mol formula | Potential Structure |
|---|---|---|---|---|
| 10.25 | 1.50 | 0.14 | 311.2, 319.2, 325.2, 339.2, (C20H36O4) 353.2 (C20H34O5) | 8-S-HETE<br>Chemical Formula: $C_{20}H_{32}O_3$<br>Exact Mass: 320.24<br>Molecular Weight: 320.47<br>m/z: 320.24 (100.0%), 321.24 (22.1%), 322.24 (2.9%)<br><br>15-(S)-HPEDA<br>Chemical Formula: $C_{20}H_{36}O_4$<br>Exact Mass: 340.26<br>Molecular Weight: 340.50<br>m/z: 340.26 (100.0%), 341.26 (21.6%), 342.27 (3.2%)<br><br>Chemical Formula: $C_{20}H_{34}O_5$<br>Exact Mass: 354.24<br>Molecular Weight: 354.48<br>m/z: 354.24 (100.0%), 355.24 (21.8%), 356.25 (2.4%), 356.24 (1.0%) |
| 11.41 | 1.67 | 0.60 | 583.4 C38H64O4 | Further investigation required to identify |
| 12.22 | 1.79 | 0.18 | 625.4 C40H66O5 | Chemical Formula: $C_{40}H_{35}O_5$<br>Exact Mass: 626.49<br>Molecular Weight: 626.95<br>m/z: 626.49 (100.0%), 627.49 (43.3%), 628.50 (10.6%), 629.50 (1.8%) |

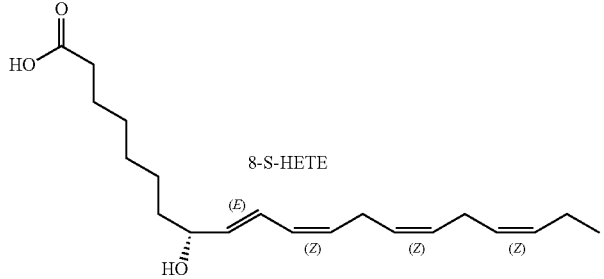
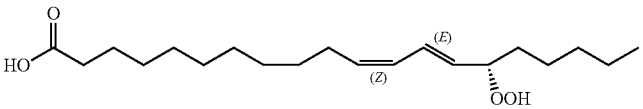
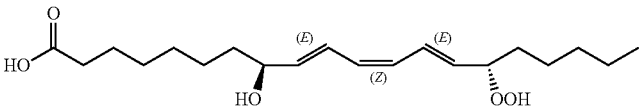
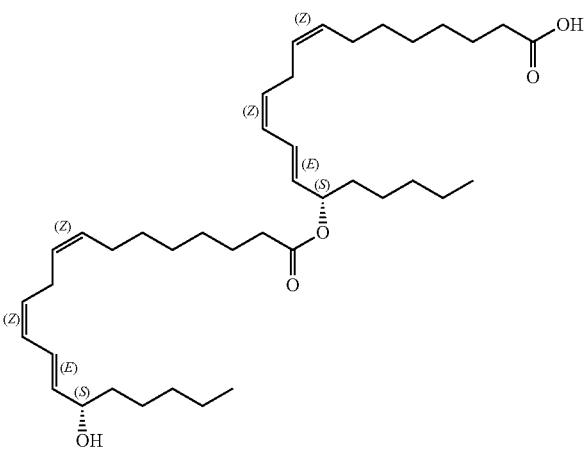

Figure 22:
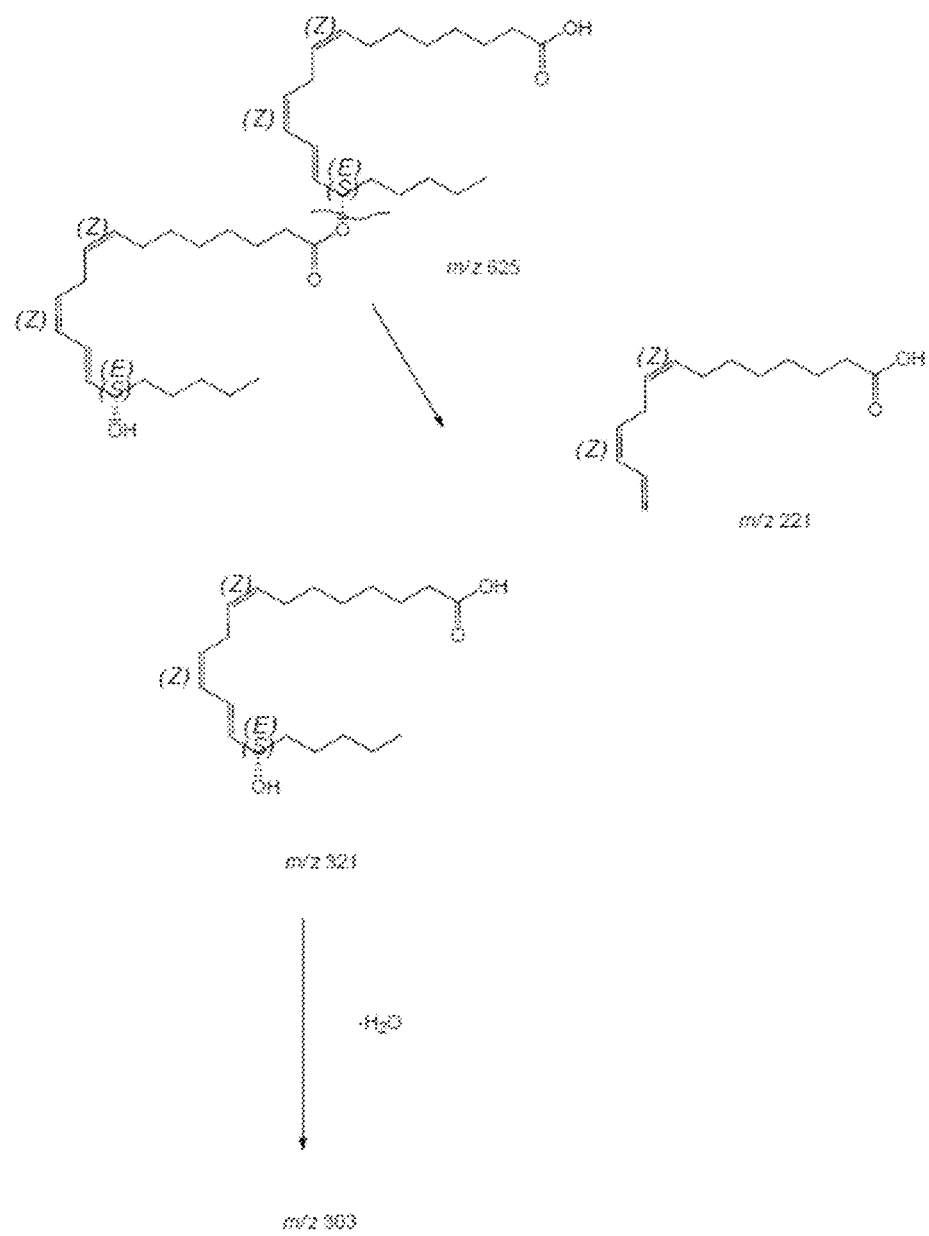
FIG. 22 proposes one possible pathway for the production of ester fragments observed by MS.

The impurity formula was $C_{40}H_{66}O_5$. The fragmentation mode supports the ester-dimer nature of the impurity. Identification by MS/MS algorithm gave daughter ions with the same profile as HETrE, which is the expected pattern from an ester cleavage (FIG. 22).

Example 22

Production of 15(S)-HEPE from EPA

The reaction was carried out by dissolved borax (194 g, 0.508 mol) in DI water (5 L) completely. L-Cysteine (40 g, 0.33 mol) and stirred for 30 minutes at 25 to 30° C. PPG-2000 (anti-foaming agent, 2 mL) was added and adjusted the reaction mass pH to 9.55-9.65 using 4M NaOH. EPA (50 g, 0.165 mol) was added and stirred for 30 minutes at 25 to 30° C. The reaction mass was cooled to 0 to 5° C. and LPX1 enzyme (1.25 g, 2.49%) was added. The reaction mixture was purged with oxygen (commercial grade, 99.5%) (1 Kg*2) and pressurized the reaction vessel with oxygen gas (2.2 Kg). The reaction mixture was stirred under oxygen pressure (2.2 Kg) at 0-5° C. for 1 hour. After complete conversion of EPA, the mass was degassed with nitrogen gas (grade-I, 1 Kg*2). L-Cysteine (20 g, 0.165 mol) was added and the reaction vessel was pressurized with nitrogen gas (grade-I, 2.2 Kg). The mass was stirred for 1 hour at 0 to 5° C. After complete conversion of peroxy intermediate, nitrogen pressure was released; the mass was unloaded from the reactor and rinsed with DM water (150 mL*2). The pH of the crude was adjusted to 3.0-4.0 using 40% w/w citric acid solution, followed by the addition of MTBE (1 L). The biphasic layers were stirred for 30 minutes and filtered. The main filtrate was taken for layer separation and the residue was washed with MTBE (500 mL*2). The residue washed MTBE was taken for extracting the separated aqueous layer. The organic layers were combined, dried over anhydrous sodium sulfate (15 g) and filtered. The filtrate was concentrated under vacuum at 30 to 35° C. to get stage-I as pale yellow liquid (48 g) with 95.00% HPLC purity. Esterification of the 15(S)-HEPE was carried out by dissolving stage-I (30 g, 0.094 mol) in dry acetone (300 mL). Potassium carbonate (68.36 g, 0.495 mol) and ethyl bromide (30.8 g, 0.283 mol) were added and the mass was stirred for 48 hours at 25-30° C. After the completion of stage-I, chilled DM water (120 mL) and brine solution (30 mL) were added to the reaction mass at 10 to 20° C. The reaction mass was brought to 25 to 30° C. and then stirred for 60 minutes. The biphasic layers were separated and the top organic layer was concentrated under vacuum at 25-30° C. to distill off the solvent. Hexanes (225 mL) was added to the crude and the mass was stirred for 30 minutes at 25-30° C. The biphasic layers were separated and the top organic layer was washed with brine solution (15%, 90 mL). The organic layer was dried over anhydrous sodium sulfate (4.5 g) and the filtered. The filtrate was added with norit charcoal (SX plus, 3 g) and stirred for 1 hour. After filtering the black solution though celite pad, the filtrate was added with silica gel (100-200 mesh, 20%) and then stirred for 1 hour. After filtering the slurry mass, the filtrate was concentrated under vacuum at 25 to 30° C. to distill off the solvent. The concentrated mass was chased with MTBE (90 mL*2) and got stage-II as pale yellow liquid (21.73 g) with 97.13% HPLC purity.

CONCLUSION AND RECOMMENDATIONS

A novel one-pot bio-oxidation/reduction of DGLA gave 15(S)-HETrE material of similar purity in a significantly increased yield (76% vs 53% for two-step methods) while using only a small fraction of the enzyme loading and much less extraction and chromatography solvents. The previous reducing agent sodium borohydride, used in sequential one-pot mode, has been substituted with cysteine used as in-situ reducing agent. This avoids hydrogen generation during the reaction and work-up, which would have been problematic on larger scale, involving long quench times potentially dangerous for quality and yield. The added advantage of the use of cysteine is that the reducing agent can be added at the beginning of the reaction, i.e. before the bio-oxidation step. Thus the generated hydroperoxide intermediate is reduced in situ as it is formed, avoiding enzyme inactivation caused by high levels of the hydroperoxide, as well as avoiding impurity formation due to over-oxidation and hydroperoxide intermediate degradation. This has resulted in the required lipoxygenase enzyme loading to be reduced by a factor of 7.6. Combined with an alternative, cheaper supply of freeze-dried enzyme, this resulted in overall reduction of the enzyme cost contribution by a factor of 15.

An enzyme source investigation alongside efforts to reduce enzyme loading requirement has revealed that lipoxygenase extracted from soy flour is now a valid enzyme source for the 15-(S)-HETrE process. It is seen as a long term option towards large scale manufacture, with a suitable soy flour removal technique yet to be developed. In the short term and for smaller, multi-kilogram manufactures it is recommended to use freeze-dried isolated enzyme, since its higher cost is offset by the non-necessity of additional soy flour processing operations.

The work-up procedure has been simplified from an emulsion forming extraction using an expensive hexane and MtBE solvent mixture to a simple slurry of the reaction precipitate with MtBE to isolate the crude product. Acidification of the reaction mixture using solid citric acid rather than a 10% solution has helped to reduce reaction volumes.

Due to the cleaner reaction profile, the column purification conditions have been modified to reduce the quantities of solvent consumed, while also replacing toxic hexane with the more benign cyclohexane. This has the added advantage of reducing processing time during solvent evaporation and thus reducing related risks of product degradation. A study of the thermal stability of 15(S)-HETrE in solution and towards exposure to hot surfaces has shown that under plant-typical solvent evaporation conditions, no significant degradation should occur on a timescale of <2 days. Ultimately, it remains to be desirable to move from column chromatography to purification by crystallization of a salt, co-crystal or other derivative in the interest of manufacturing cost reduction towards large scale >100 kg.

The new processing method has included handling the material under inert atmosphere at all suitable stages, in an effort to reduce oxygen exposure and thus the generation of peroxides and subsequent decomposition products. The peroxide values obtained are now in the region of 10-15 compared with values of 90+ obtained previously. Results from the stability trial suggest that the initial quality of material has had a positive effect on the observed stability (discounting formation of esters).

Attempted identification of the major impurities (>0.10% area) in the purified material by LC-MS suggests that they are mainly derived from the starting DGLA. A self-esterified product is also observable, the quantity of which increases over time at higher temperatures (>−20° C.). The status of impurity identification is sufficient for early phase clinical testing and related manufacturing.

The process as currently designed does not display any significant thermal hazards—a slight temperature rise is observed when the reaction mixture reaches 40° C., but as the temperature will be maintained between 0-5° C., this will not be an obstacle for safe process scale up.

In conclusion, the developed process resulting from this program of work is now fit for purpose for safe and robust early phase multi-kilogram scale up manufacture conforming to cGMP.

| Parameter | Initial Un-optimised Process | Optimised Process | Comment |
|---|---|---|---|
| | | Advantages | |
| Product Yield | 40-50% | 74% | Significant yield improvement reduces DGLA and enzyme requirements |
| Reducing Agent | Sodium Borohydride | Cysteine | Advantages of cysteine<br>One step oxidation/reduction reaction leading to reduced hydroperoxide degradants<br>No hydrogen generated during reduction reaction<br>has anti oxidant properties leading to reduced hydroperoxide degradants<br>Prevents excess hydroperoxide formation reducing enzyme loading |
| Enzyme Loading | 13.7 munits/g | 1.8 munits/g | Due to reduced enzyme inactivation by hydroperoxide intermediate enzyme loading reduced<br>Using freeze dried enzyme (£0.42/munit) instead of liquid enzyme (£0.83/m/unit) in combination with lower loading requirement resulted in cost reduction from £11.37/g DGLA to £0.75/g DGLA |
| Purity | 96.0-97.5% | >97% | Due to reduction in formation of oxidation impurities, a higher product purity is achievable |
| Chromatography Solvents | 19 L/column | 11 L/column | Due to lower impurity formation, purification solvent requirements reduce 1.7 fold |

The invention claimed is:

1. A process for the production of a 15-hydroxy derivative of a fatty acid comprising, oxidizing a fatty acid under an oxygen atmosphere of about 1.1 bar to about 4 bar to form a 15-hydroperoxy fatty acid intermediate and reducing at least a portion of the 15-hydroperoxy fatty acid intermediate using a reducing agent to form a 15-hydroxy derivative of the fatty acid.

2. The process according to claim 1, wherein the step of oxidizing comprises contacting the fatty acid with less than 400 M units of enzyme per gram of the fatty acid.

3. The process according to claim 1, producing yield of the 15-hydroxy derivative of the fatty acid of at least about 50%.

4. The process of claim 1, wherein the 15-hydroxy derivative is 15(S)-HETrE.

5. The process of claim 1, wherein the 15-hydroxy derivative is 15(S)-hydroxyeicosapentaenoic acid.

6. The process of claim 1, wherein the reducing agent comprises cysteine.

7. The process of claim 1, wherein the fatty acid comprises DGLA.

8. The process of claim 1, wherein the fatty acid comprises a polyunsaturated fatty acid.

9. The process of claim 1, wherein the 15-hydroxy derivative of the fatty acid has a purity not less than 95% wt/wt.

10. The process of claim 1, wherein the batch size is not less than 100 kg.

11. The process of claim 1, wherein the batch size is not less than 250 kg.

12. The process of claim 1, wherein the batch size is not less than 500 kg.

13. The process of claim 1, wherein the oxidizing comprises contacting the fatty acid with a soy flour extract.

14. The process of claim 13 further comprising:
contacting soy flour with a buffer solution at pH 4.5 to produce a crude soy flour extract; and
filtering the crude soy flour extract to produce the soy flour extract.

15. The process of claim 14, wherein the soy flour extract has an activity comparable to about 2 mg/mL of purified, freeze-dried lipoxygenase enzyme.

* * * * *